(12) United States Patent
Mamigonians

(10) Patent No.: US 11,238,260 B2
(45) Date of Patent: Feb. 1, 2022

(54) EXAMINING OBJECTS USING ELECTRIC FIELDS

(71) Applicant: Zedsen Limited, London (GB)

(72) Inventor: Hrand Mami Mamigonians, London (GB)

(73) Assignee: Zedsen Limited, London (GB)

( * ) Notice: Subject to any disclaimer, the term of this patent is extended or adjusted under 35 U.S.C. 154(b) by 83 days.

(21) Appl. No.: 16/865,469

(22) Filed: May 4, 2020

(65) Prior Publication Data

US 2020/0349331 A1 Nov. 5, 2020

(30) Foreign Application Priority Data

May 4, 2019 (GB) ..................................... 1906386

(51) Int. Cl.
| | |
|---|---|
| *G01R 27/26* | (2006.01) |
| *G06K 9/00* | (2006.01) |
| *G01N 27/22* | (2006.01) |

(52) U.S. Cl.
CPC ......... *G06K 9/0002* (2013.01); *G01N 27/228* (2013.01)

(58) Field of Classification Search
USPC ................................ 324/600, 658, 660–663
See application file for complete search history.

(56) References Cited

U.S. PATENT DOCUMENTS

| | | | |
|---|---|---|---|
| 5,551,288 A | 9/1996 | Geraldi et al. | |
| 8,866,491 B2* | 10/2014 | Ksondzyk | G06F 3/0418 |
| | | | 324/601 |
| 8,994,383 B2 | 3/2015 | Mamigonians | |
| 2010/0292945 A1* | 11/2010 | Reynolds | G06F 3/04166 |
| | | | 702/65 |
| 2019/0328311 A1* | 10/2019 | Mamigonians | A61B 5/4312 |

* cited by examiner

*Primary Examiner* — Vincent Q Nguyen
(74) *Attorney, Agent, or Firm* — Cooper Legal Group, LLC

(57) ABSTRACT

Non-biological objects, biological specimens and living tissues are examined using electric fields to identify regions of differing permittivity and conductivity. Substantially parallel electrodes are deployed in capacitive alignment with an object and energization pulses are generated for application to any of the electrodes as a transmitter. Output signals from any remaining electrode are monitored, in which a peak value of an output signal is indicative of permittivity and a decay rate of an output signal is indicative of conductivity. A first set of n electrodes (one to fifteen) is selected, each of which is capacitively coupled with a second set of m electrodes (two to eight) that are the nearest neighbouring electrodes to an electrode selected from the first set.

15 Claims, 25 Drawing Sheets

LAYER 7

| | T1 : R8 | T2 : R9 | T3 : R10 | T4 : R11 | T5 : R12 | T6 : R13 | T7 : R14 | T8 : R15 |
|---|---|---|---|---|---|---|---|---|
| 1411 | | | | | | | | |
| 1412 | | | | | | | | |
| 1413 | | | | | | | | |
| 1414 | | | | | | | | |
| 1415 | | | | | | | | |

Fig. 25

EXAMINING OBJECTS USING ELECTRIC FIELDS

CROSS REFERENCE TO RELATED APPLICATIONS

This application claims priority from United Kingdom Patent Application number 1906386.6, filed on May 4, 2019, the whole contents of which are incorporated herein by reference.

BACKGROUND OF THE INVENTION

The present invention relates to an apparatus for examining objects using electric fields to identify regions of differing permittivity and conductivity. The present invention also relates to a method of examining objects (including non-biological objects, biological specimens and living tissues) using electric fields.

It is known to examine objects using electric fields, as described in U.S. Pat. No. 8,994,383 assigned to the present applicant. However, problems arise when examining objects that are not homogeneous, such as biological specimens and living tissues.

It is also known to adjust the penetration of electric fields by selecting differing combinations of transmitter electrode and receiver electrode, with differing separation distances. Thus, as the distance between a transmitter electrode and a receiver electrode increases, a greater level of penetration is possible from deploying a technique that may be referred to as "layering".

U.S. Pat. No. 5,551,288 shows a layering technique in which capacitive coupling is achieved between a first electrode and a second electrode, between the first electrode and a third electrode and then between the first electrode and a fourth electrode. A region, of an aircraft wing in this example, may be examined by repeating this pattern for groups of similar electrodes. Thus, within each group, one electrode is selected as an electrode in common which is then capacitively coupled with the other three electrodes in each respective group. However, problems arise when deploying this approach in alternative environments, given that the amount of information available from each layer is derived from a different part of the object.

BRIEF SUMMARY OF THE INVENTION

According to a first aspect of the present invention, there is provided an apparatus for examining objects (including non-biological objects, biological specimens and living tissues) using electric fields to identify regions in a said object of differing permittivity and conductivity, comprising: a plurality of substantially parallel electrodes mounted on a substrate, wherein said electrodes are coated with an insulator allowing them to be brought into contact with an object and thereby be in capacitive alignment with said object; a generator for generating energization pulses and a de-multiplexer for applying said energization pulses to any of said electrodes as a transmitter; a monitor for monitoring output signals and a multiplexer for connecting any one of said electrodes to said monitor; and a processor, wherein said processor is configured to: select a first set of n electrodes from said plurality of substantially parallel electrodes; establish capacitively coupled electrode pairs, in which each of said first set of n electrodes is capacitively coupled with a second set of m electrodes from said plurality of substantially parallel electrodes, wherein each said second set of m electrodes are the nearest neighbouring electrodes to an electrode selected from said first set of n electrodes; and the number of electrodes present in said second set of m electrodes represents a degree of layering.

It is possible for the level of energization to remain substantially constant. However, an embodiment comprises an energizing circuit for energizing a transmitter electrode to a level determined by said processor, wherein said processor adjusts the level of energizing with reference to the degree of layering.

In an embodiment, an analog-to-digital converter samples the output signal, to produce an output data set. However, other techniques could be deployed for obtaining digital values or a greater level of signal processing could be performed in the analog domain.

In some situations, an instantaneous out is all that may be required. However, in an embodiment, the apparatus further comprises a storage device for storing said output data set; and a transmission device for transmitting said output data set.

Many procedures could be deployed for analysing the output data, possibly involving calculations derived from a mathematical model. However, in an embodiment, the apparatus further comprises a machine-learning system for receiving said output data set to produce extent data for a substance of interest present within the object.

According to a second aspect of the present invention, there is provided a method of examining objects (including non-biological objects, biological specimens and living tissues) using electric fields to identify regions in said object of differing permittivity/conductivity, comprising the steps of: deploying a plurality of substantially parallel electrodes in capacitive alignment with said object; generating energization pulses for application to any of said electrodes as a transmitter electrode; monitoring output signals from any remaining one of said electrodes as a receiver electrode, wherein a peak value of an output signal is indicative of permittivity and a decay rate of an output signal is indicative of conductivity, such that during each energization operation, an energized transmitter electrode and a monitored receiver electrode define a capacitively coupled electrode pair; selecting a first set of n electrodes from said plurality of substantially parallel electrodes; and establishing capacitively coupled electrode pairs, in which each of said first set of n electrodes is capacitively coupled with a second set of m electrodes from said plurality of substantially parallel electrodes; wherein each said second set of m electrodes are the nearest neighbouring electrodes to an electrode selected from said first set of n electrodes; and the number of electrodes present in said second set of m electrodes represents a degree of layering.

In an embodiment, the step of establishing capacitively coupled electrode pairs comprises the steps of: sequentially selecting each said n electrode of said first set as an electrode in common; and for each said selected electrode in common, sequentially defining capacitively coupled electrode pairs with a second set of m nearest neighbouring electrodes. However, other patterns of selection may be deployed in order to generate the required capacitive couplings. Similarly, in an embodiment said step of sequentially selecting each said first set of n electrodes comprises the steps of: selecting a first end electrode as an electrode in common; sequentially selecting adjacent electrodes as electrodes in common in a first direction of dynamic layering until a second end electrode is reached; selecting said second end electrode as an electrode in common; sequentially selecting adjacent electrodes as electrodes in common in a second direction of dynamic layering until said first end is reached; and selecting a set of m electrodes for each electrode in common that are nearest neighbours only in the direction of dynamic layering.

In an embodiment, the method further comprises the step of sampling each output signal produced from each capacitively coupled electrode pair to produce a coupling data set, wherein a first sample of each coupling data set is indicative of permittivity and subsequent samples of each coupling data set are indicative of conductivity. In an alternative embodiment, only a single sample is taken and this may be at the peak value or elsewhere.

Each coupling data set may be associated with a degree of layering. However, alternative data structures are possible. The step of selecting the first set of n electrodes may comprise the step of selecting all of said plurality of substantially parallel electrodes.

Additional procedures may be included to locate the position of an object before performing a layering operation. Thus, in an embodiment, the step of selecting a first set of n electrodes comprises the steps of: identifying capacitively aligned electrodes that are at the position of an object; and selecting said capacitively aligned electrodes as said first set of n electrodes.

It is possible for an additional set of electrodes to be included that are displaced and isolated from the first set. In an embodiment, the plurality of substantially parallel electrodes represents a first group of substantially parallel electrodes;

a further layering procedure is performed with respect to a second group of substantially parallel electrodes; and said second group is substantially orthogonal to said first group.

In some embodiments, it may be possible to obtain useful output data without performing a specific calibration procedure or the calibration procedure may differ from the test procedure. However, in an embodiment, a first layering procedure is performed with no object present to generate calibration data, prior to similar layering procedures being performed when an object is present to produce test data.

Many procedures are possible for obtaining useful output results. However, in an embodiment, the method further comprises the steps of: producing plural learning output data sets for a first group of objects, for which the extent to which a substance under investigation is present is known; deploying said plural learning output data sets to prepare a machine-learning system; and analysing live output data sets by means of said machine-learning system to produce respective extent data for said substance.

Embodiments of the invention will be described, by way of example only, with reference to the accompanying drawings. The detailed embodiments show the best mode known to the inventor and provide support for the invention as claimed. However, they are only exemplary and should not be used to interpret or limit the scope of the claims. Their purpose is to provide a teaching to those skilled in the art. Components and processes distinguished by ordinal phrases such as "first" and "second" do not necessarily define an order or ranking of any sort.

BRIEF DESCRIPTION OF THE SEVERAL VIEWS OF THE DRAWINGS

FIG. 25 illustrates the data produced with respect to layer 7 identified in FIG. 24.

DETAILED DESCRIPTION OF EMBODIMENTS OF THE INVENTION

FIG. 1

Figure 1:
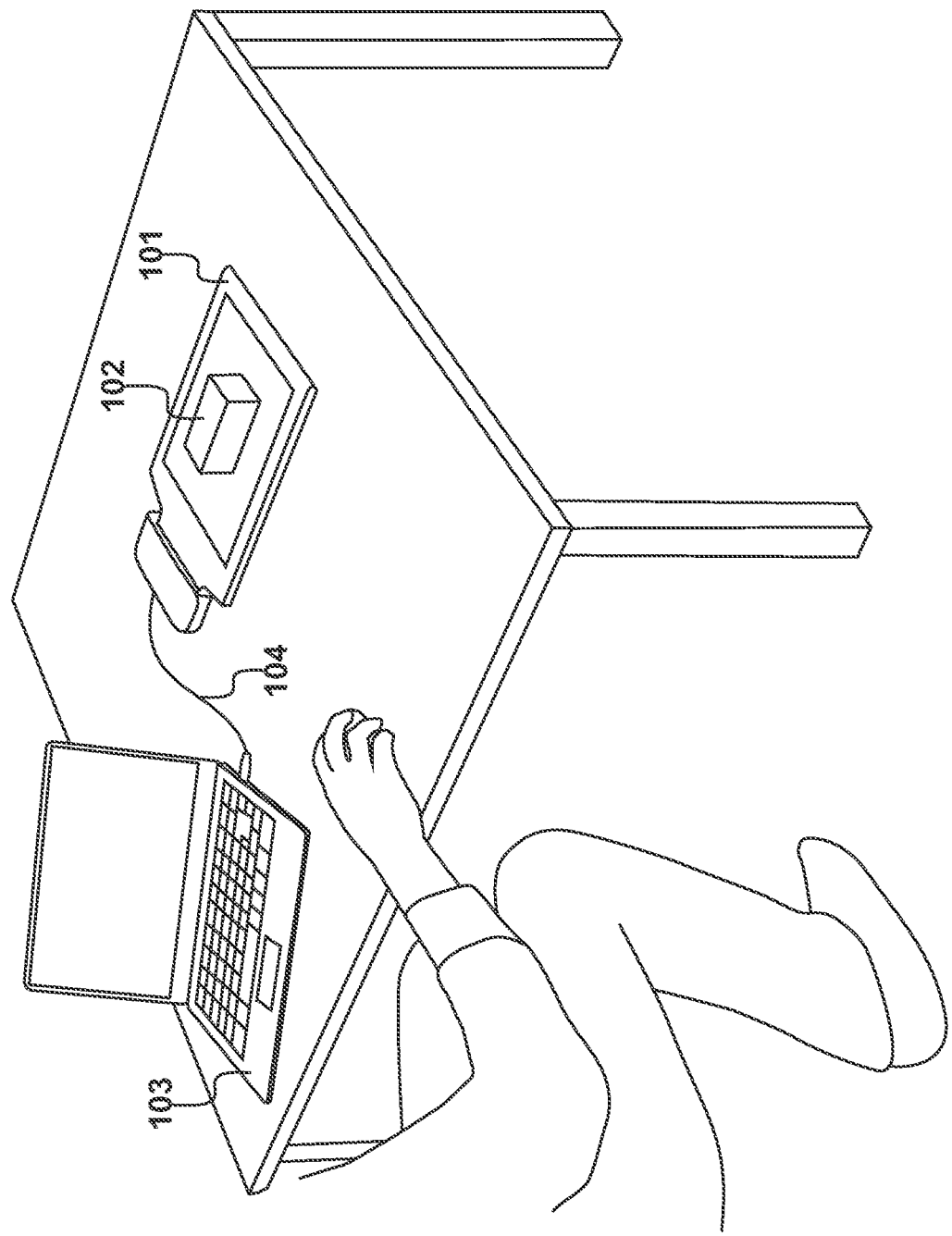
FIG. 1 shows an examination apparatus.

An examination apparatus 101 is shown in FIG. 1, for examining the electrical properties (permittivity and conductivity) of objects, such as an object 102, using electric fields. In this example, the object being examined is a non-biological object that may, for example, consist of organic substances, non-organic substances or a mixture of both secured within a container.

In this embodiment, the examination apparatus 101 communicates with a data-processing system 103 via a data communication cable 104, possible designed in accordance with established USB protocols.

FIG. 2

Figure 2:
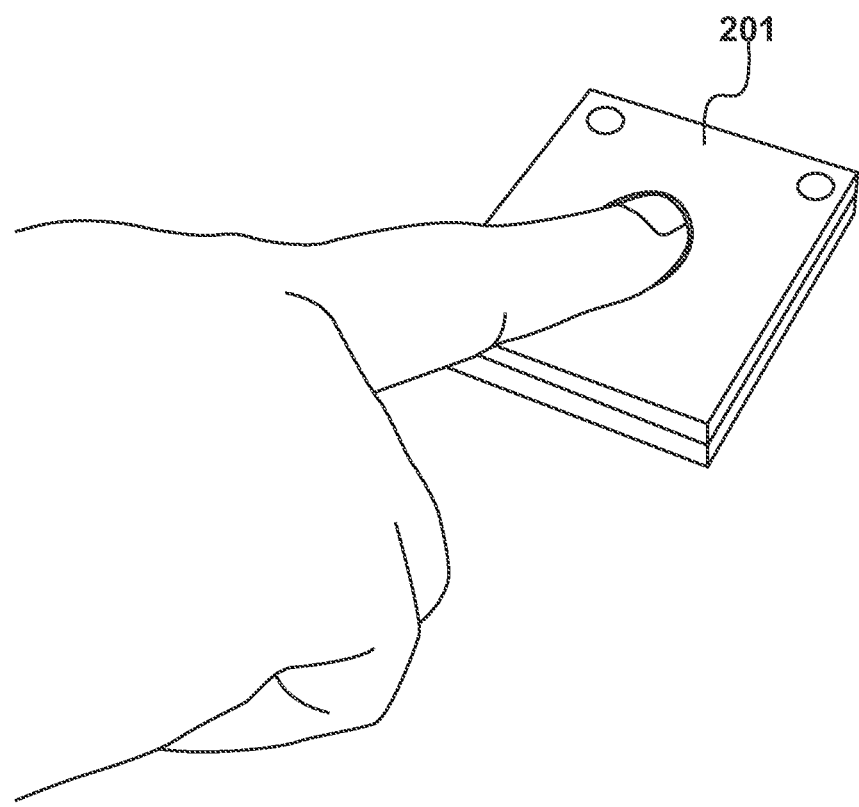
FIG. 2 shows a first alternative examination apparatus.

A first alternative examination apparatus is shown in FIG. 2, that is designed to examine living-tissue objects. In this example, a finger is placed on an electrode-supporting membrane. The finger is examined to evaluate levels of one or more blood constituents, given the high volume of blood capillaries at finger ends along with their relative closeness to the skin.

Many blood constituents may be identified, including glucose. However, research conducted by the inventor shows that a sufficiently rich data set is required if the accuracy of glucose concentration measurement is to compete with established invasive procedures.

FIG. 3

Figure 3:
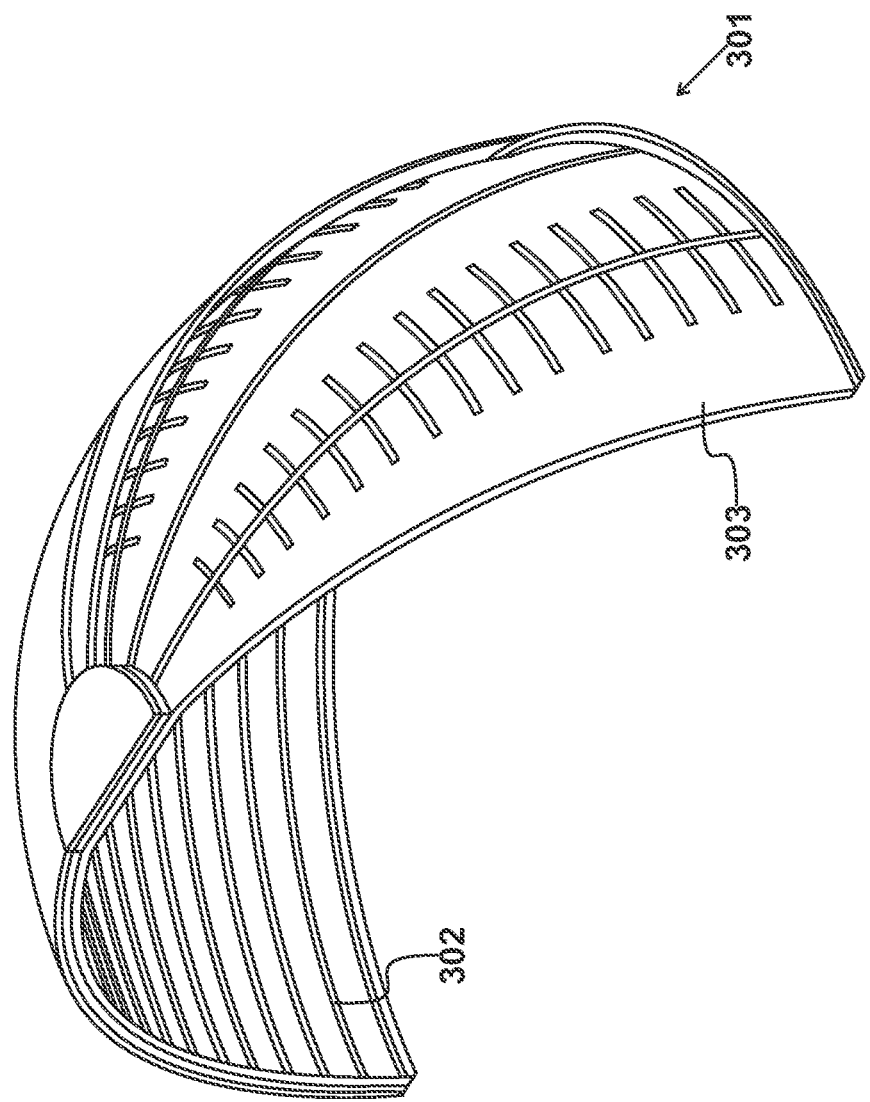
FIG. 3 shows a second alternative examination apparatus.

A sub-assembly 301 of a second alternative examination apparatus is shown in FIG. 3, that has been specifically developed to examine breast tissue, particularly with a view towards identifying early-stage tumours. Thus, like apparatus 201, this is directed towards the examination of living tissue but can also be deployed for the examination of biological specimens.

The use of the word "object" as used herein is therefore intended to include non-biological items (both organic and non-organic), biological specimens and living tissue. The object is assumed to be complex (not homogeneous) requiring a large output data block to identify constituents within regions of interest.

All three examples of an examination apparatus (101, 201, 301) deploy a plurality of substantially parallel electrodes (302) mounted on a substrate (303). The electrodes are coated with an insulator, thereby allowing them to brought into contact with an object and thereby be in capacitive alignment with the object. As used herein, "capacitive alignment" means that electric fields generated by transmitter electrodes and monitored by receiver electrodes pass through the object, such that the monitored response is influenced by the material content of the object.

During capacitive alignment, capacitive coupling occurs between a transmitter electrode and a receiver electrode, such that the selected electrodes may be identified as a capacitively coupled pair. In the embodiments, the transmitter electrode is energized by a sharply rising pulse, producing a dynamic electric field. The electric field passes through the object causing polarized molecules to align with the field, permitting the establishment of a field within the object, due to polarisation, as the transmitter voltage rises. This results in the creation of an electrical potential within the object, which will then decay due to resistive leakage.

Thus, an output signal, induced in the receiver electrode, is monitored and will have a peak value predominantly determined by the permittivity of the object and a rate of decay determined predominantly by the conductivity of the object. Multiple sampling of monitored output signals captures a rich data set that is influenced by both the permittivity and conductivity of the object.

In the first and second embodiments, the parallel electrodes are straight, allowing a second similar set of electrodes to be included on the opposite side of a membrane, that are substantially orthogonal to the first set. However, in the third embodiment, the geometry of the parallel electrodes is different, in that they define parallel concentric circles.

All embodiments include multiplexing and de-multiplexing devices that allow any of the available electrodes to be selected as a transmitter or as a receiver. A processor is configured to select a first set of n electrodes from the plural substantially parallel electrodes and establish capacitively coupled electrode pairs, in which each of the first set of n electrodes is capacitively coupled with a second set of m electrodes selected from the first set. Furthermore, each of the second set of m electrodes are the nearest neighbouring electrodes to an electrode selected from said first set of n electrodes and the number m of electrodes present in the second set represents a degree of layering.

FIG. 4

Figure 4:
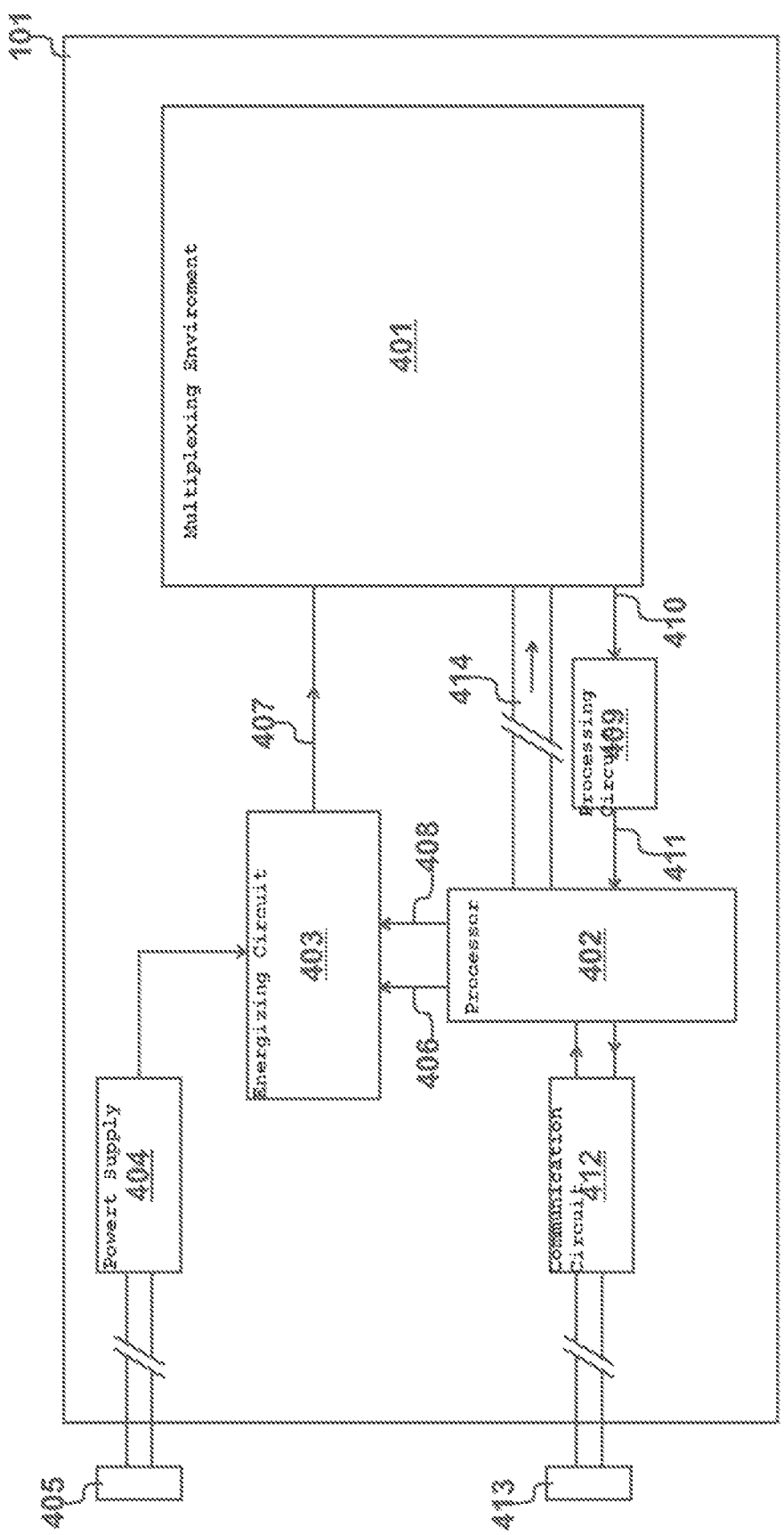
FIG. 4 shows a schematic representation of an examination apparatus.

A schematic representation of an examination apparatus embodying the present invention is shown in FIG. 4. A multiplexing environment 401 includes a dielectric membrane supporting at least one set of parallel electrodes. Environment 401 also includes a de-multiplexer for de-multiplexing energizing input pulses, along with a multiplexer for combining selected output signals.

A processor 402, implemented as a microcontroller, addresses the de-multiplexer and the multiplexer to ensure that the same electrode cannot be both energized as a transmitter and monitored as a receiver during the same coupling operation. An energizing circuit 403 is energized by a power supply 404 that may in turn receives power from an external source via a power input connector 405. A voltage-control line 406 from the processor 402 to the energizing circuit 403, allows processor 402 to control the voltage (and hence the energy) of the energizing signals supplied to the multiplexing environment via a strobing line 407. The timing of each energizing signal is controlled by the processor 402 via a trigger-signal line 408.

An output from the multiplexing environment 401 is supplied to an analog-processing circuit 409 over a first analog line 410. A conditioning operation is performed by the analog-processing circuit 409, allowing analog output signals to be supplied to the processor 402 via a second analog line 411. The processor 402 also communicates with a two-way-data-communication circuit 412 to facilitate the connection of the data-communication cable to a data interface 413.

During scanning operations, the processor 402 supplies addresses over an address bus 414 to the multiplexing environment 401, to define a pair of capacitively coupled electrodes. An energization operation is performed by applying an energizing voltage to strobing line 407, monitoring a resulting output signal and sampling the output signal multiple times to capture data indicative of a peak value and a rate of decay.

FIG. 5

Figure 5:
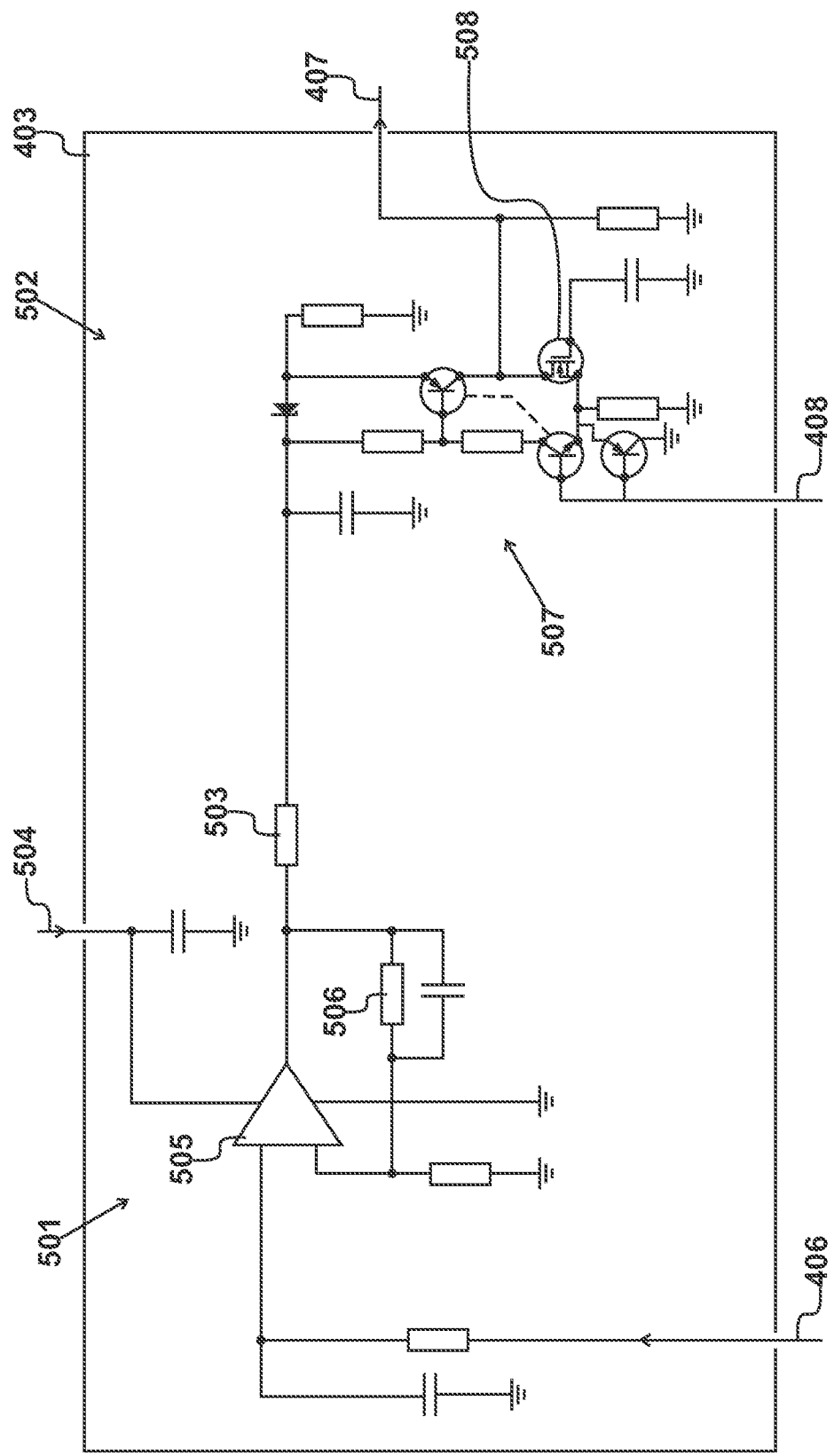
FIG. 5 shows a schematic representation of an energizing circuit, of the type identified in FIG. 4.

A schematic representation of the energizing circuit 403 is shown in FIG. 5. The energizing circuit includes a voltage-control circuit 501 connected to a strobing circuit 502 via current-limiting resistor 503. A voltage-input line 504 receives energizing power from the power supply to energize an operational amplifier 505. Operational amplifier 505 is configured as a comparator and receives a reference voltage via a feedback resistor 506. This is compared against a voltage-control signal received on the voltage-control line 406, to produce an input voltage for the strobing circuit 502.

The strobing circuit includes two bipolar transistors configured as a Darlington pair 507, in combination with a MOSFET (metal oxide silicon field effect transistor) 508. This creates energizing pulses with sharp rising edges, that are conveyed to the strobing line 407, after receiving a trigger signal on line 408.

FIG. 6

Figure 6:
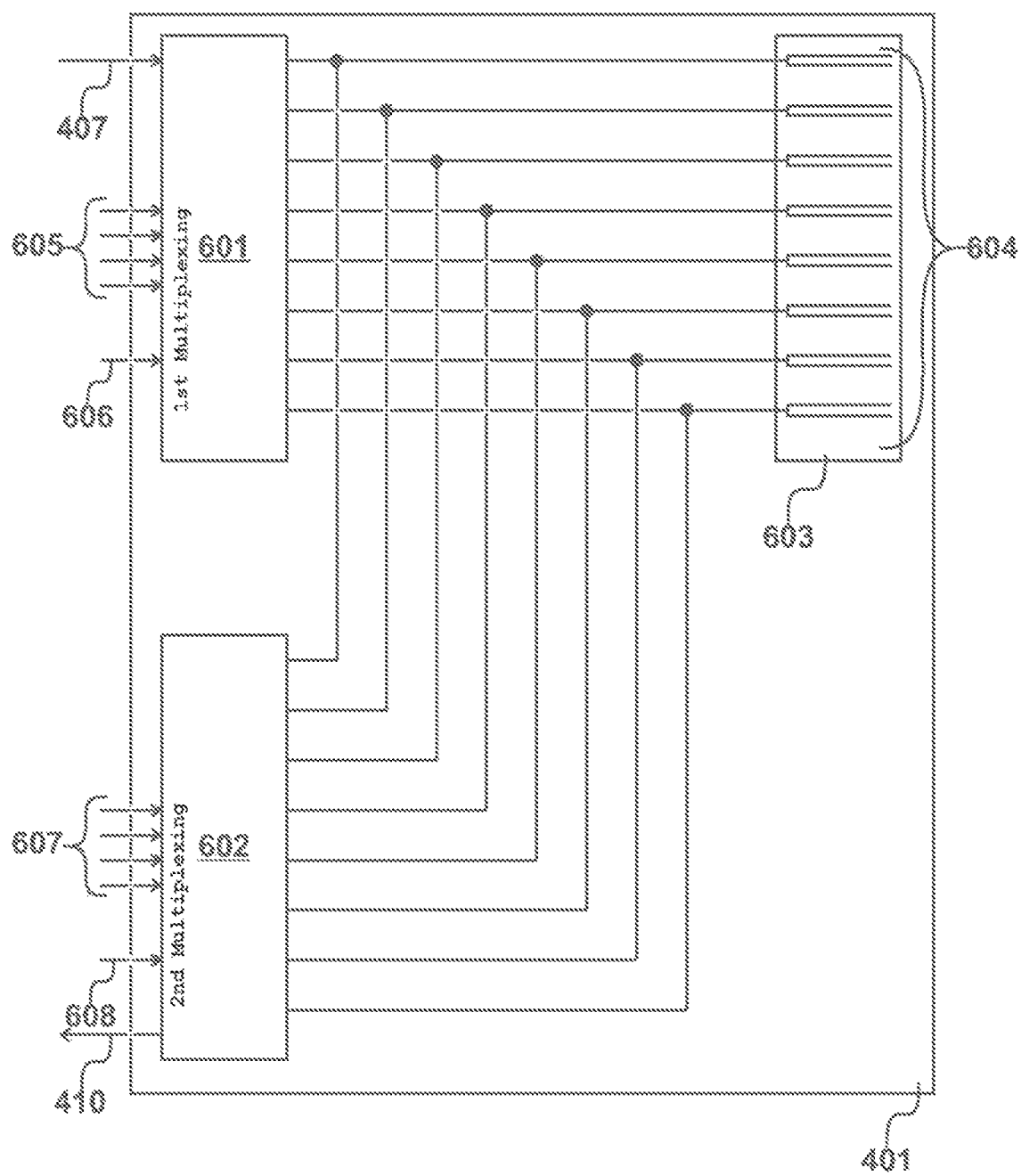
FIG. 6 shows an example of the multiplexing environment identified in FIG. 4.

An example of a multiplexing environment is shown in FIG. 6, in which a first multiplexing device 601 supplies energizing input signals to a selected transmitter electrode, while a second multiplexing device 602 monitors output signals from a selected receiver electrode. A dielectric membrane 603 supports plural parallel electrodes coated with an insulating coating to allow them to be brought into contact with an object. Eight linear electrodes 604 are shown for illustrative purposes but more or fewer electrodes may be included. The first alternative embodiment, the operation of which will be described in greater detail, includes fifteen electrodes, for example.

Embodiments may also include a second set of electrodes, as described with reference to FIG. 7, to provide measurement in two dimensions; with the second set of electrodes being provided with respective multiplexing devices.

The first multiplexing device 601 includes first address lines 605 and an enabling line 606. Similarly, the second multiplexing device 602 includes second address lines 607 and a second enabling line 608. During each electrode coupling operation, addresses are supplied to the address busses but line selection does not occur until respective enabling signals have been received.

FIG. 7

Figure 7:
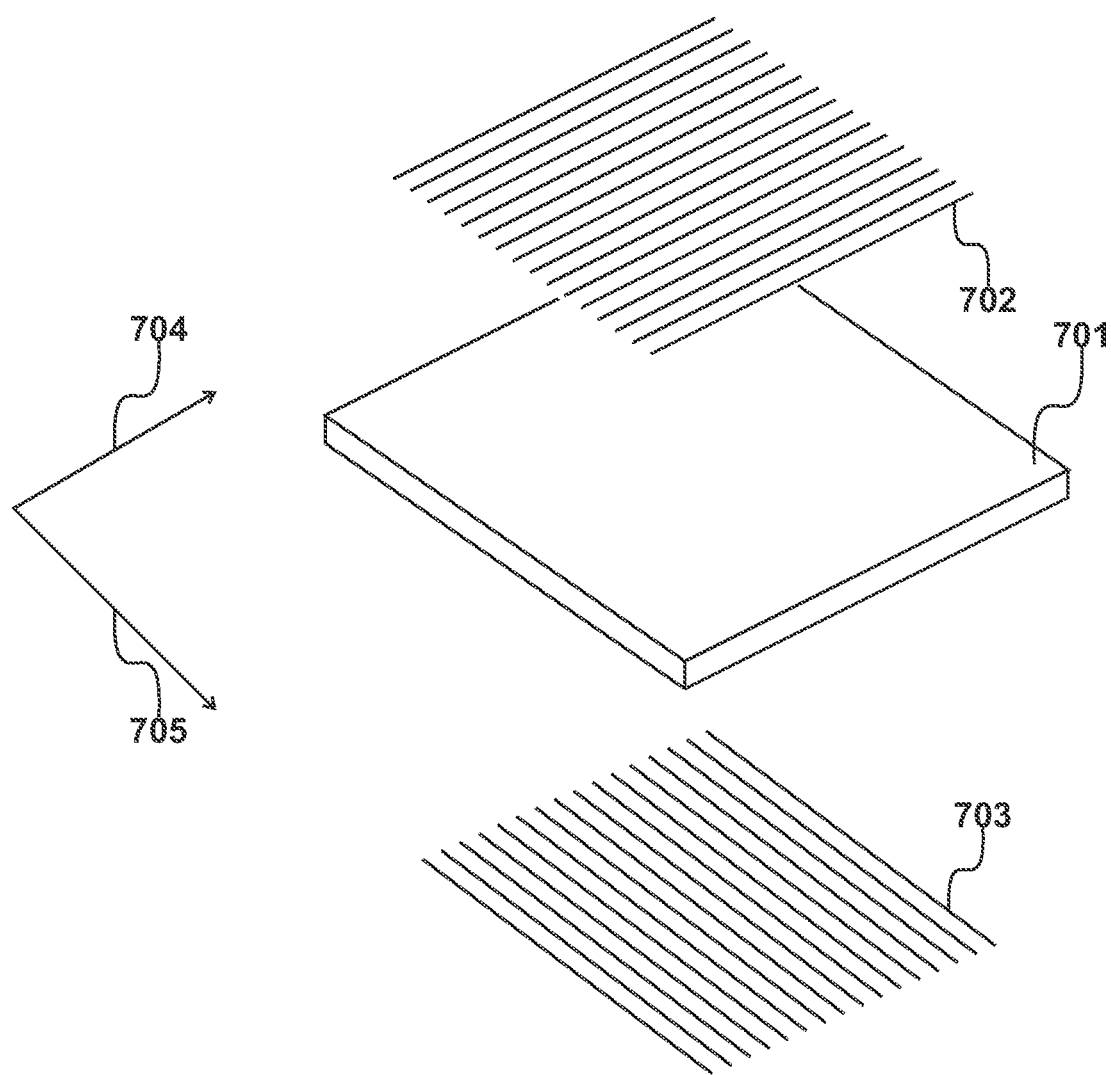
FIG. 7 illustrates two mutually orthogonal electrode sets.

The provision of two mutually orthogonal electrode sets is illustrated in FIG. 7. A dielectric membrane 701 is of the type used in the first alternative examination apparatus 201, as described with reference to FIG. 2. The sub-assembly includes a first group of electrodes 702, along with a second group of electrodes 703. In this example, fifteen electrodes are provided in each group and for each group, the electrodes are substantially linear and substantially parallel. However, they are arranged in mutually orthogonal orientations. Thus, the first group of electrodes 702 may be considered as being aligned in an x dimension, illustrated by a first arrow 704. Similarly, the second group of electrodes 703 may be considered as being aligned in a y dimension, as illustrated by a second arrow 705.

Layering is achieved by coupling electrodes of a first set (selected from a group) and then repeating a scanning operation by coupling electrodes in the second set, selected from the same group. Thus, layering operations performed by the first group of electrodes 702 achieve a layering operation in the direction of the second arrow 705. Similarly, the second group of electrodes 703 achieve a similar layering operation in the direction of the first arrow 704.

FIG. 8

Figure 8:
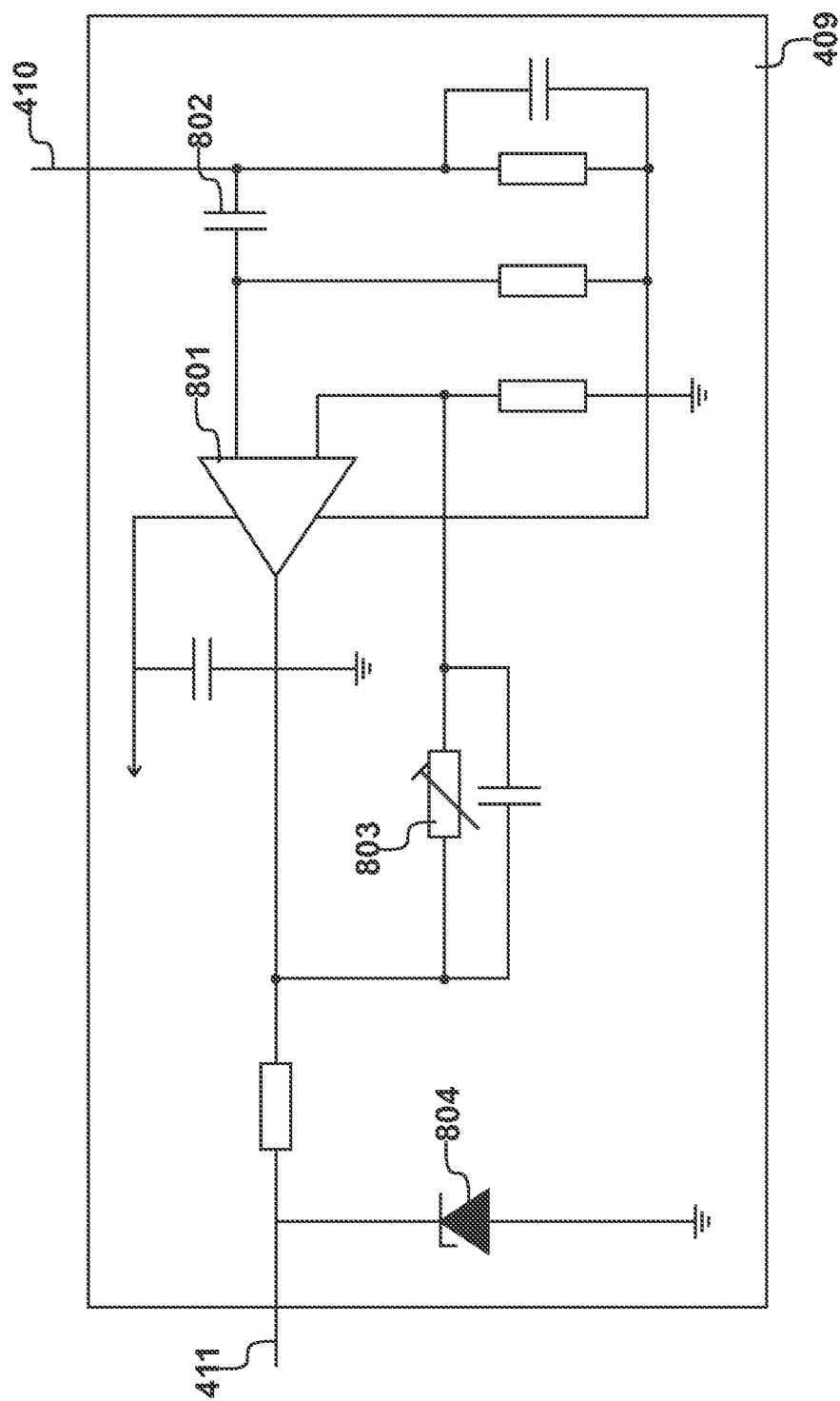
FIG. 8 shows an example of the analog processing circuit identified in FIG. 4.

Analog-processing circuit 409 is shown in FIG. 8. Signals received on the first analog line 410 are supplied to a buffering amplifier 801 via a decoupling capacitor 802. During an initial set-up procedure, a variable feedback resistor 803 is trimmed to optimize the level of monitored signals supplied to the processor 402 via the second analog line 411. A Zenner diode 804 prevents excessive voltages being applied to the processor 402.

FIG. 9

Figure 9:
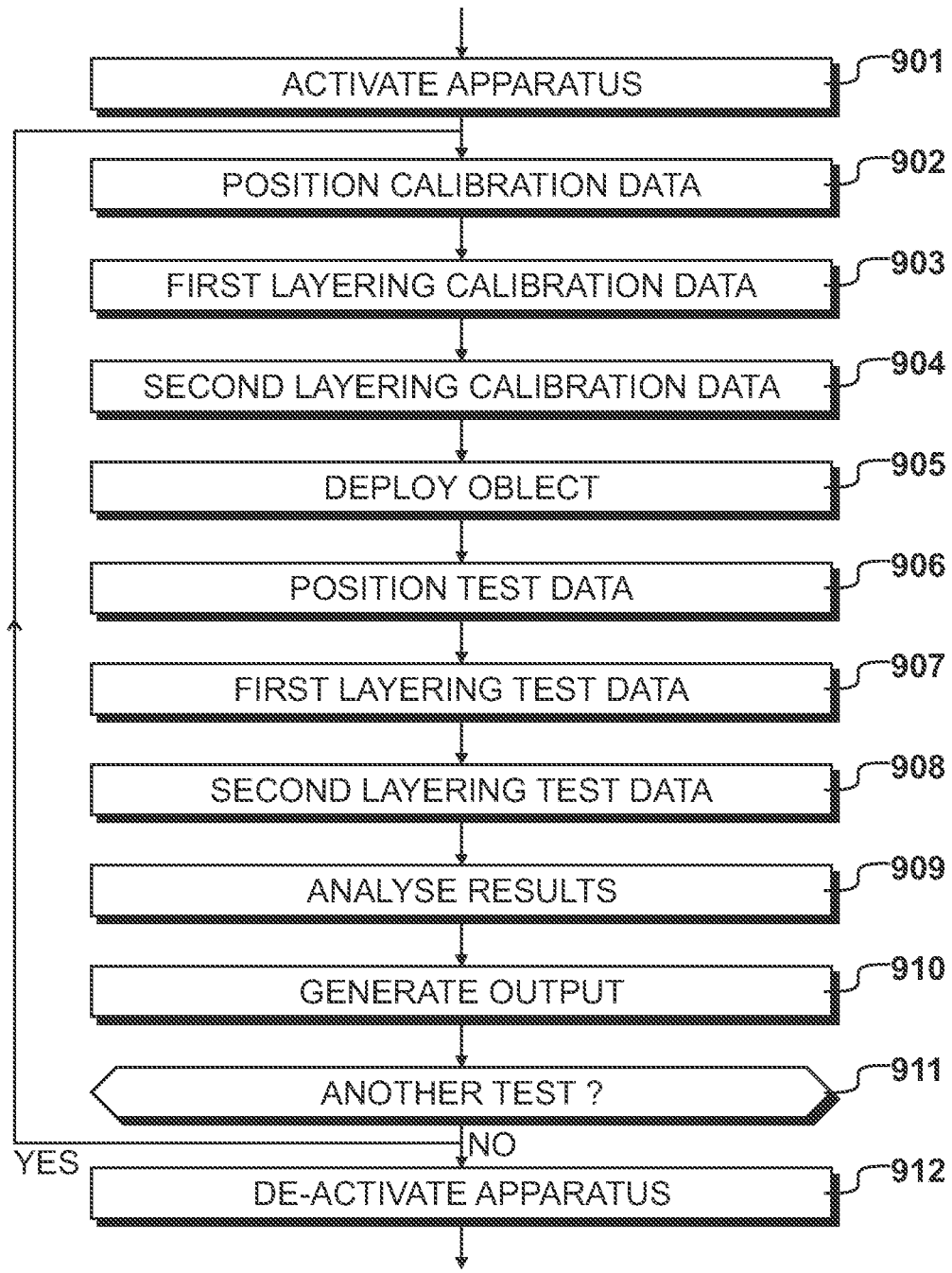
FIG. 9 shows procedures performed by the processor identified in FIG. 4.

Procedures performed by the processor 402 are shown in FIG. 9. At step 901, the examination apparatus is activated but at this stage the apparatus is not placed in contact with an object. Prior to actual test data being produced, a calibration procedure is conducted during which all of the test procedures are performed without an object being present. Thus, calibration is achieved by comparing the actual test results against similar results produced with respect to the surrounding air.

In this embodiment, the procedures are appropriate for the first alternative examination apparatus described with reference to FIG. 2. The apparatus is provided with a first group of parallel electrodes, along with a second group of orthogonal parallel electrodes, as described with reference to FIG. 7. This facilitates the adoption of three separate scanning operations. In a first operation, position data is produced which will in turn provides an indication of the actual location of an object upon the electrode array. In accordance with known techniques, capacitive coupling is achieved between electrodes of the first group 702 and the second group 703. Thus, a first electrode of the first group is selected which is then sequentially capacitively coupled to all of the electrodes in the second group. The second electrode of the first group is then selected and again it is capacitively coupled with all of the electrodes of the second group. Thus, this procedure is repeated until all of the electrodes of the first group 702 have been capacitively coupled with all the electrodes of the second group 703, thereby generating a matrix of capacitive-coupled data. However, it should be noted that this data is not produced by penetrating electric fields to varying depths in the z dimension.

Figure 13:
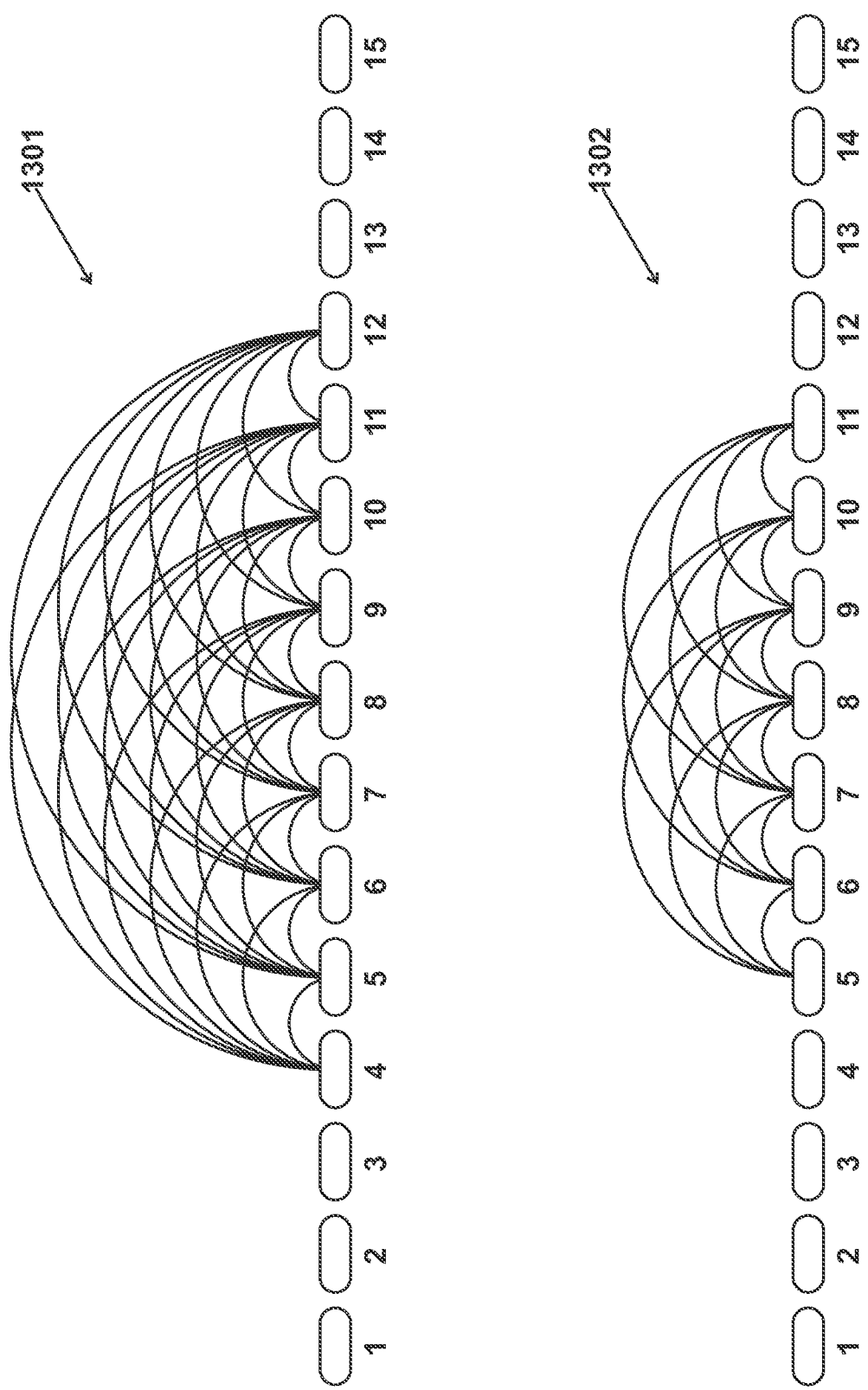
FIG. 13 shows patterns similar to that shown in FIG. 12 in which fewer electrodes are selected as the first set.

Position data may be used to provide graphical indications as to the presence of an object and may also be used, in combination with the layering data, to identify properties of the object. Furthermore, in an alternative embodiment, the nature of the subsequent layering procedures may be modified, as described with reference to FIG. 13, in response to the positional data collected in the two-dimensional x, y plane.

Thus, at step 902 position calibration data is produced, as described above, followed by the production of first layering calibration data at step 903 and the production of second layering calibration data at step 904.

During the production of the first layering calibration data, only the first group of electrodes 702 are deployed, resulting in electric fields being generated in the direction of second arrow 705. Similarly, when the second layering calibration data is being produced, only electrodes in the second group 703 are capacitively coupled, resulting in the generation of electric fields in the direction of first arrow 704. Thus, position data relates to the two-dimensional x, y plane, first layering data relates to linear results in the y dimension and the second layering data relates to linear results in the x direction.

At step 905, the object is deployed. Thus, in the embodiment of FIG. 1, object 102 would be placed on the examination apparatus 101. In the example of FIG. 2, a finger would be placed over the examination apparatus 201, as illustrated in FIG. 2. Similarly, with reference to the second alternative embodiment described with reference to FIG. 3, the membrane is contained within an examination apparatus that may be identified as being substantially bra shaped, which is located to allow electric fields to penetrate breast tissue.

The procedure is now in a position to produce test data. Thus, at step 906 position test data is produced, using a procedure substantially similar to that performed at step 902. Thereafter, at step 907 first layering test data is produced, followed by second layering test data being produced at step 908. These procedures are substantially similar to procedures 903 and 904 respectively.

Results are analysed at step 909 and output data is generated at step 910. A question is then asked at step 911 as to whether another test is to be performed and when answered in the affirmative, new position calibration data is generated at step 902. Alternately, if the question asked at step 911 is answered in the negative, the apparatus is deactivated at step 912.

FIG. 10

Figure 10:
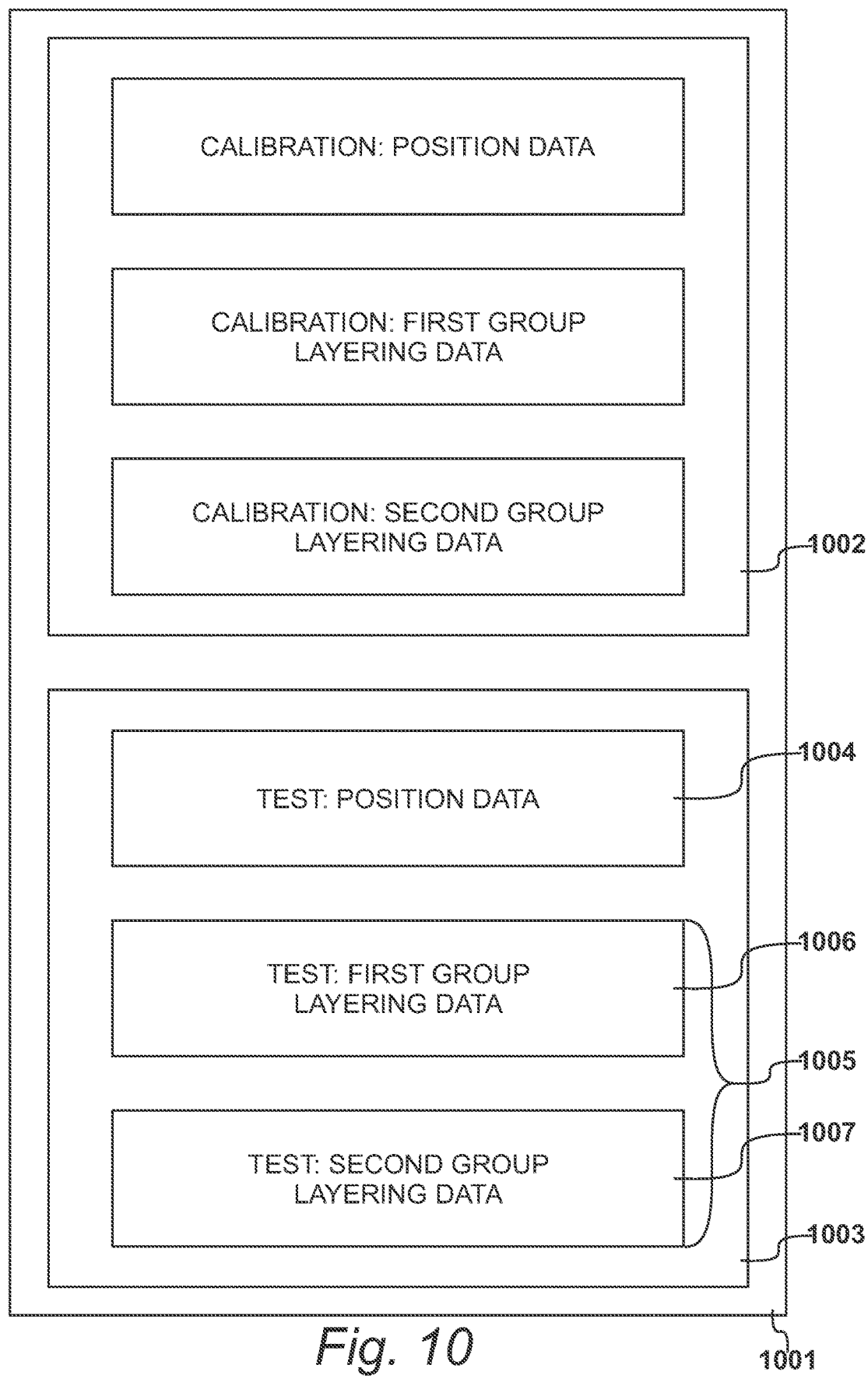
FIG. 10 illustrates an output data block of the type produced by the procedures identified in FIG. 9.

The procedures described with reference to FIG. 9 produce an output data block 1001, as shown in FIG. 10. Each output data block consists of calibration data 1002 and test data 1003. The test data 1003, for example, includes test position data 1004 and test layering data 1005.

When two groups of electrodes are present, as described with reference to FIG. 7, the test layering data 1005 comprises a first layering data set 1006 and a second layering data set 1007. As illustrated in FIG. 10, the calibration data also includes a similar data structure.

FIG. 11

In an embodiment, the analysing step 909, described with reference to FIG. 9, is achieved using a machine learning system. In this embodiment, plural learning output data blocks are produced for a first selection of objects, for which the extent to which a substance under investigation is present is known.

Plural learning output data blocks are deployed to prepare a machine learning system. Live output data blocks are then analysed, at step 909, by means of the machine learning system, to produce respective extent data for the substance under investigation.

Machine learning systems of this type deploy regression algorithms to produce continuous outputs which, for example, may identify the level of glucose present within blood capillaries of the finger. In an alternative embodiment, a classification algorithm may be deployed to identify whether, for example, a glucose level is too low, normal of too high.

As is known in the art, each training example is represented by a vector and the training data is presented in a matrix. Through iterative operation of an objective function, supervised learning algorithms learn a function that can be used to predict the output associated with new inputs. Thus, an optimized function allows the algorithm to correctly determine the output for inputs that were not part of the original training data.

Furthermore, after a training procedure, the system will have learnt to perform the task required and it is therefore possible, for example, to provide an accurate indication of the level of glucose present in blood, the level of other constituents present in blood, the presence of tumours in tissue or the nature of material contained within non-biological objects.

Figure 11:
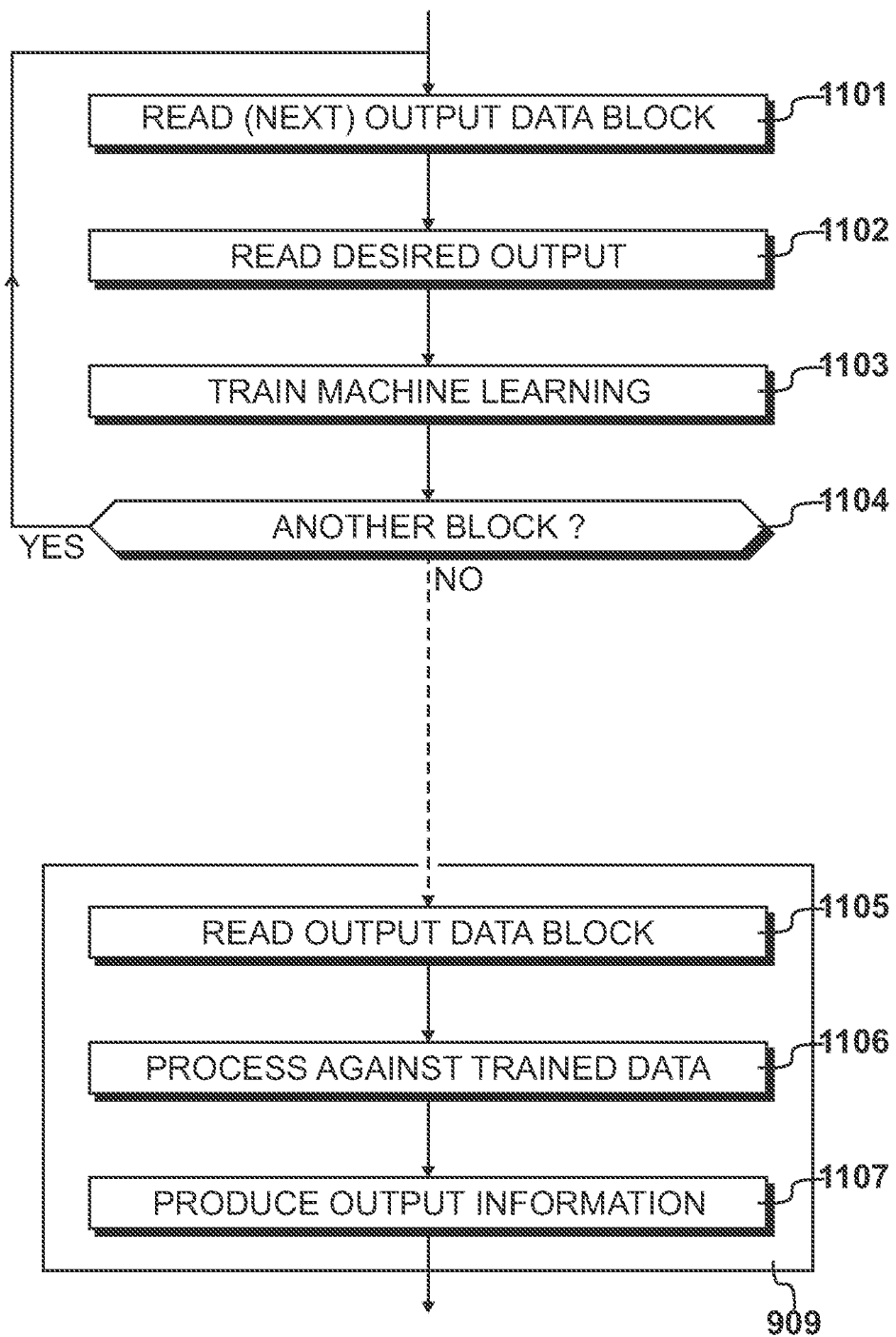
FIG. 11 illustrates operations performed by a machine learning system.

Operations performed with respect to the machine learning system are shown in FIG. 11. Steps 1101 to 1104 relate to the training of the system, whereafter steps 1105 to 1108 relate to the deployment of the system.

At step 1101, the next output data block, having a structure of the type described with reference to FIG. 10, is read and the related desired output is then read at step 1102. Thus, during the training operation, it is necessary to make measurements using alternative procedures. Thus, for example, when training a glucose monitoring apparatus, glucose measurements are made using conventional invasive techniques.

At step 1103 the machine learning system is trained in response to the data received at step 1101 and step 1102, whereafter at step 1104, a question is asked as to whether another block is to be considered. When answered in the affirmative, the next output data block is read at step 1101.

As is known in the art, the accuracy of the system will improve with the number of iterations that are possible and this will be dependent upon the availability of data. During this process, random tests can be conducted to determine the accuracy of the system and a convergence towards accurate results should be witnessed. Only when an appropriate convergence has been achieved is it then possible to progress to the next stage.

Thus, the next stage represents procedures performed at step 909. Again, an output data block, of the type described with reference to FIG. 10, is read at step 1105. At step 1106, this data block is processed against the trained data produced by the procedures described above. Thereafter, at step 1107, output information is produced and from this an appropriate output results is generated at step 910.

FIG. 12

The embodiments described herein facilitate a method of examining objects, including non-biological objects, biological specimens and living tissues, using electric fields to identify regions of differing permittivity and conductivity. The method involves deploying a plurality of substantially parallel electrodes in capacitive alignment with an object. For the purposes of this example, the plurality of substantially parallel electrodes may be identified as the first group of electrodes 702, supported within the first alternative examination apparatus 201. In this example, the object is living tissue and the procedure produces the first layering data set 1006.

Figure 12:
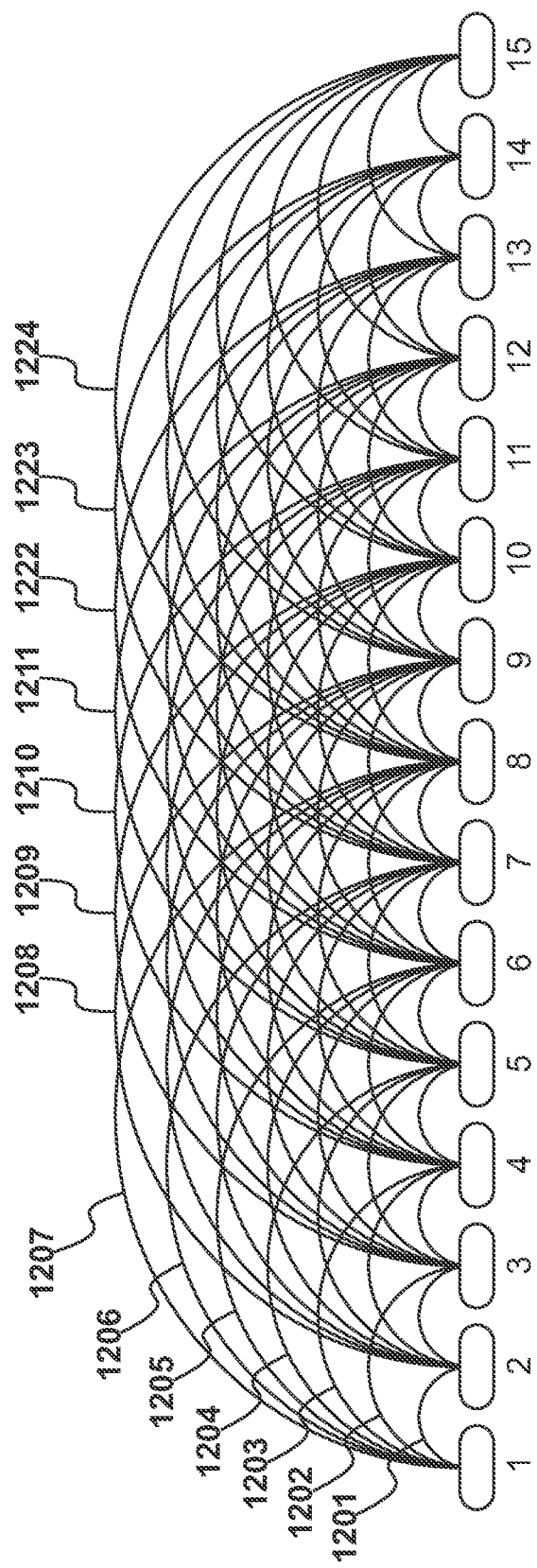
FIG. 12 shows a pattern of electric fields generated from a plurality of electrodes embodying the present invention.

The electrodes of the first set 702 are shown in FIG. 12, numbered 1 to 15. Electronics within the examination apparatus 201, of the type described with reference to FIG. 4, generates energization pulses for application to any of the electrodes 1 to 15 as a transmitter electrode. In addition, output signals may be monitored from any remaining one of the electrodes as a receiver electrode, wherein a peak value of an output signal is indicative of permittivity and a decay rate of an output signal is indicative of conductively. Thus, during each energization operation, an energized transmitter electrode and a monitored receiver electrode define a capacitively coupled electrode pair.

From the available electrodes 1 to 15 of the selected group, a first set of n electrodes is selected. Thus, in the example shown in FIG. 12, all fifteen electrodes are selected as the first set of n electrodes. However, it is not necessary for all of the available electrodes to be selected in this way, so the selected set may contain fewer electrodes than the selected group. Alternative selections will be described with reference to FIG. 13.

Capacitively coupled electrode pairs are established, in which each of the first set of n electrodes is capacitively coupled with a second set of m electrodes selected from the first set of n electrodes. Thus, the second set of m electrodes is a subset of the first set of n electrodes. Thus, for each selected electrode of the first set, a respective second set of m electrodes is identified. These m electrodes are capacitively coupled with the selected electrode of the first set.

In an embodiment, this capacitive coupling may occur in parallel, requiring multiple analog to digital conversion devices operating in parallel. However, in this embodiment, capacitive coupling occurs sequentially such that, at any instant, only one electrode of the first set is coupled with one electrode of the second set. To achieve this coupling, either electrode may be energized as a transmitter, with the other electrode of the pair being monitored as the receiver. Furthermore, each second set of m electrodes are the nearest neighbouring electrodes to an electrode selected from the first set of n electrodes. Consequently, the number of electrodes present in the second set of m electrodes represents a degree of layering.

Following this method, all of the resulting electric fields are illustrated in FIG. 12. The first set of n electrodes consists of all fifteen available electrodes within the group 702. The degree of layering is seven, as illustrated by electric fields 1201 to 1207. Each of the first set of n electrodes is capacitively coupled with a second set of n electrodes. Thus, when considering the first electrode 1 as being a member of the first set, it is capacitively coupled with electrodes 2 to 8. Electrode 1 is not capacitively coupled with electrodes 9 to 15. Thus, the second set of m electrodes (2 to 8) with reference to the first electrode 1, are the nearest neighbouring electrodes to electrode 1, selected from the remaining n electrodes of the first set. Thus, having achieved a seventh degree of layering, it would be necessary to couple electrode 1 with electrode 9, should an eighth degree of layering be required.

The order in which electrodes are selectively coupled is not particularly relevant, provided that all electric fields illustrated in FIG. 12 are realised. Duplication may occur if, for example, electrode one is initially selected as a transmitter with electrode two selected as a receiver, whereafter, electrode two is selected as the transmitter and electrode one is selected as the receiver. At the end of the cycle, coupling between electrode one and electrode two has occurred twice and in some embodiments, when this happens, the results may be averaged. There is, however, no requirement, for example, to couple electrode one with electrode eleven.

Previous investigations have identified advantages with respect to having multiple couplings with the end electrodes which, in this example, are identified as electrode 1 and electrode 15. Such an approach achieves a degree of layering. However, in the present embodiment, many more layering opportunities are established through a dynamic process. The embodiments described herein develop these techniques to collect the required data in a systematic way and this approach will be described with reference to FIGS. 15 to 23. However, it should be appreciated that other approaches may be adopted to achieve the result of deriving data from coupling m electrodes that are the nearest neighbouring electrodes to an electrode selected from the first set of n electrodes.

As previously described, data derived from the seventh degree of layering is achieved by electric field 1207, from the coupling of electrode 1 with electrode 8. Similar seventh degree fields are shown at 1208 (coupling electrodes 2 and 9), 1209 (coupling electrodes 3 and 10), 1210 (coupling electrodes 4 and 11), 1211 (coupling electrodes 5 and 12), 1212 (coupling electrodes 6 and 13), 1213 coupling electrodes 7 and 14) and 1214 (coupling electrodes 8 and 15).

FIG. 13

In an embodiment, it is possible for the test position data 1004 to identify the actual position of the object, such that this data may be used to reduce the number of coupling operations that are required. In the example shown at 1301, all fifteen electrodes are present but the first set of n electrodes only consists of electrodes 4 to 12. Again, however, a layering degree of seven is achieved, because electrode 4 couples with electrode 11 and electrode 5 couples with electrode 12, etc. Thus, the first set is selected such that n is equal to nine, whereafter second sets are selected in which m is equal to seven.

A similar illustration is shown at 1302 and again all fifteen electrodes are available in the group. However, on this occasion, only electrodes 5 to 11 have been selected for the first set, therefore n is equal to seven. Each electrode within this first set is then coupled with its five nearest neighbours, such that m equals five and the degree of layering is therefore five.

FIG. 14

It can be appreciated that to achieve dynamic layering, a significant number of coupling operations are required for each scanning procedure, as described with reference to FIG. 12. Furthermore, each output signal produced from each capacitively coupled electrode pair is sampled to produce a coupling data set, in which a first sample of each coupling data set is indicative of permittivity and subsequent samples of each coupling data set are indicative of conductively.

Figure 14:
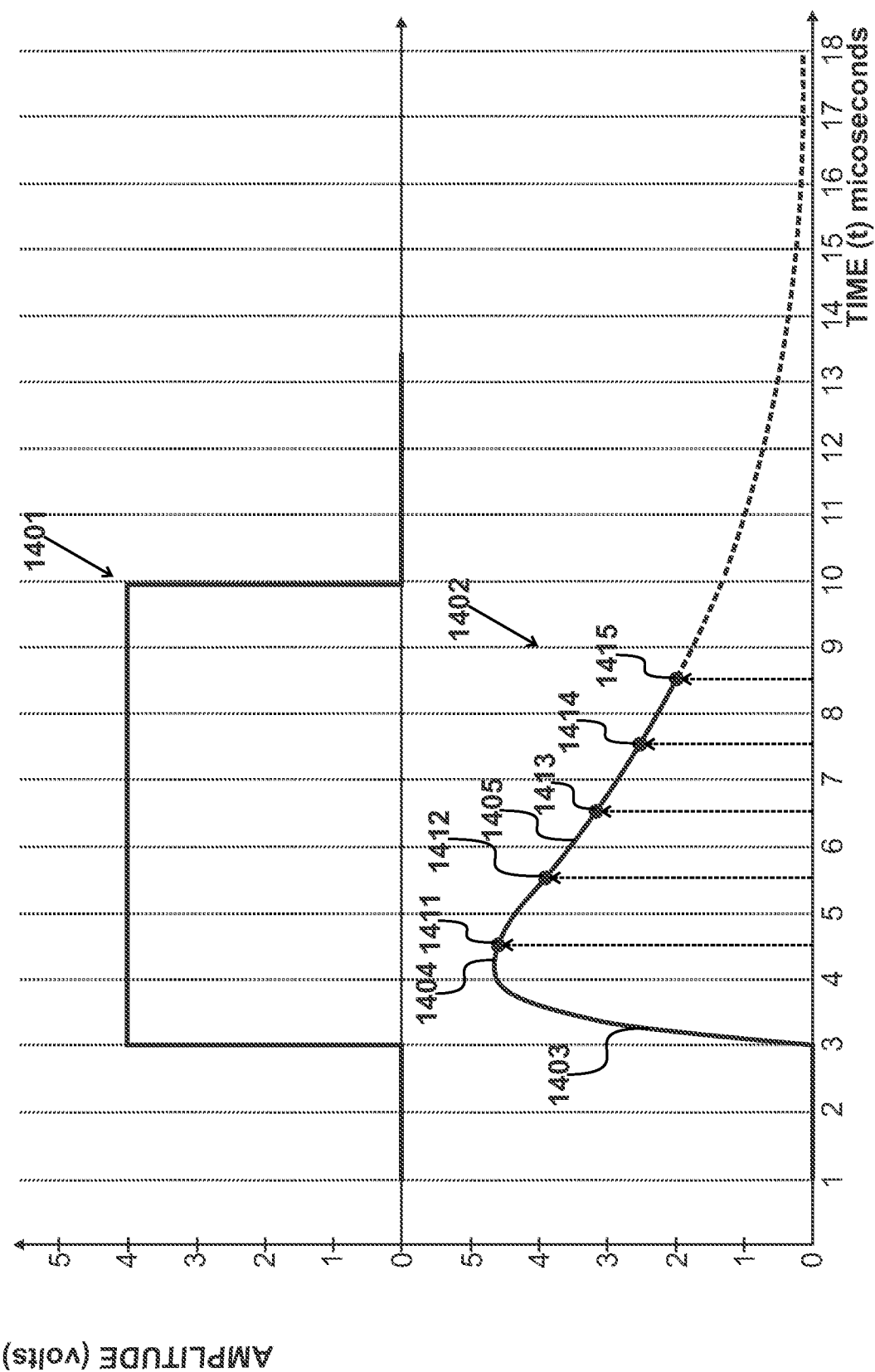
FIG. 14 shows the relationship between an energizing input pulse and a monitored output signal.

An energizing input pulse 1401 is shown in FIG. 14, plotted on a shared time axis with a monitored output signal 1402. The energizing input pulse 1401 rises relatively sharply to increase the high frequency components and hence produce a high-frequency-dependent response characteristic. In this embodiment, a frequency response is achieved without being required to sweep through many sinusoids of different frequencies.

The monitored output signal 1402 has been amplified by the circuit described with reference to FIG. 8 and is then sampled by an analog-to-digital convertor forming part of the processor 402. The monitored output signal 1402 has a rising edge 1403, a peak 1404 and a falling edge 1405. The peak level 1404 will be determined predominantly by permittivity characteristics of the object. Similarly, the falling edge 1405 represents a decay of the induced field and the rate of decay will be determined predominantly by the conductivity of the object. Thus, by recording multiple samples, it is possible to obtain rich coupling data samples within each coupling data set. To achieve this, as illustrated in FIG. 14, a first sampling point 1411 is followed by a second sampling point 1412, followed by a third sampling point 1413, a fourth sampling point 1414 and a fifth sampling point 1415.

The processor 402 is responsible for initiating the energization input signal, therefore the processor is instructed with an appropriate delay period before initiating the sampling process. This delay is determined empirically and aims to place the first sampling point at the peak value. However, a degree of tolerance is permitted, as illustrated in FIG. 14, given that the same delay period is used for each coupling operation, allowing comparisons to be made between similar examples. However, for the purposes of this embodiment, it should be appreciated that each coupling operation results in the generation of an output signal substantially similar to that shown at 1402, which in turn generates a coupling data set containing five data points. In other embodiments, more or fewer data samples may be recorded.

FIG. 15

As previously described with reference to FIG. 12, the present embodiment aims to capacitively couple electrodes to establish the pattern shown in FIG. 12. The actual order for doing this is not relevant but the present embodiment takes a systematic approach to facilitate the programming of processor 402. In particular, in an embodiment, capacitively coupled electrode pairs are established by sequentially selecting each of the n electrodes of the first set as an electrode in common. Furthermore, for each selected electrode in common, the procedure sequentially defines capacitively coupled electrode pairs with the second set of m nearest neighbouring electrodes. Thus, as illustrated in FIG. 15, a procedure may start by selecting electrode 1 as the first electrode in common and then sequentially capacitively coupling electrode 1 with the m nearest neighbouring electrodes, which are electrodes 2 to 8, when layering to the seventh degree is required.

Figure 15:
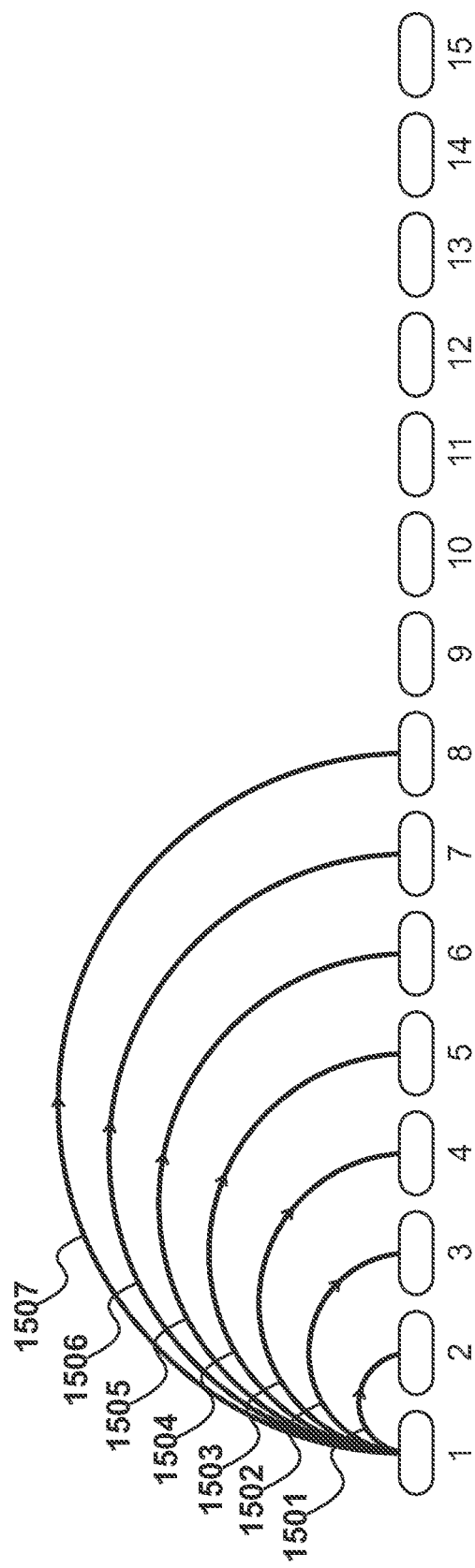
FIG. 15 illustrates an embodiment for achieving the pattern identified in FIG. 12, in which a first electrode is energized.
Figure 16:
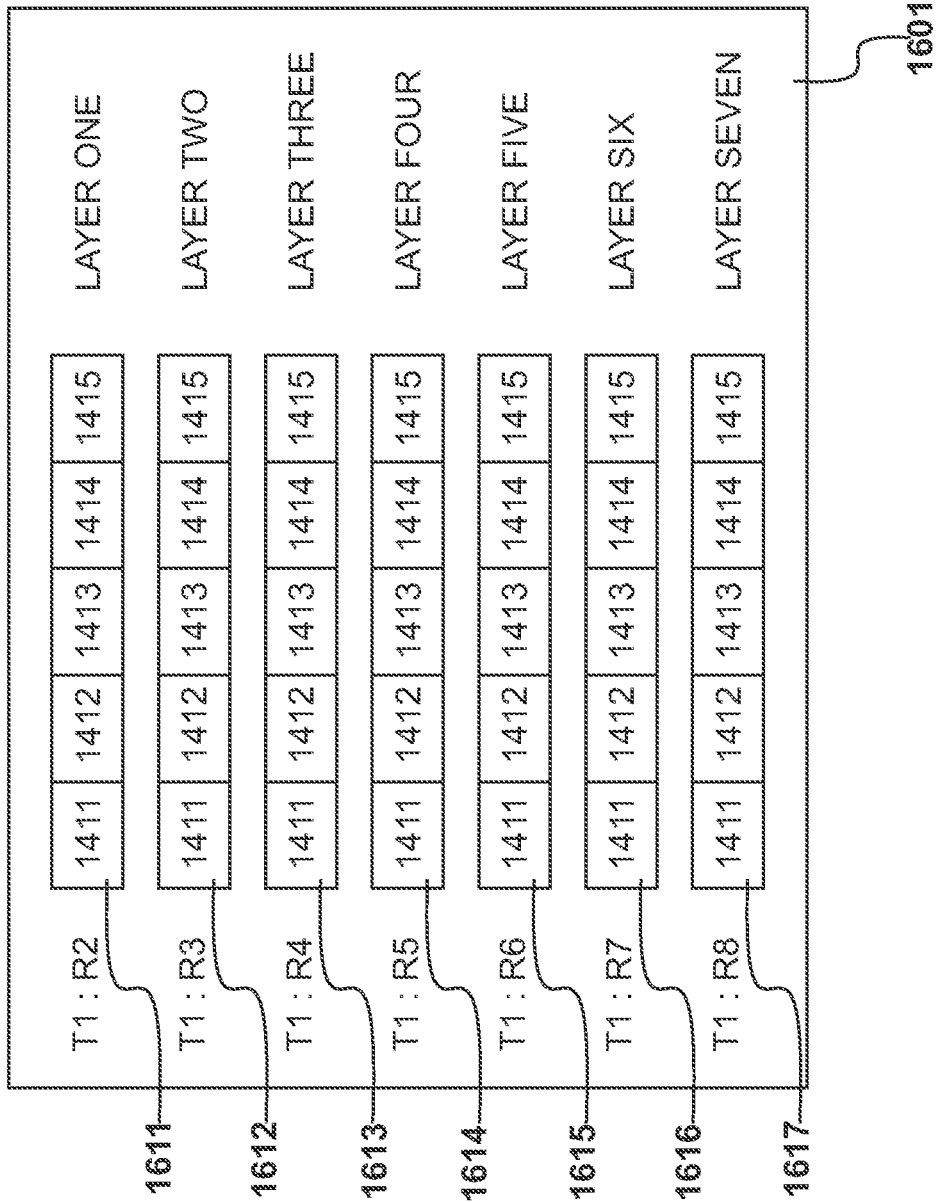
FIG. 16 shows a common electrode data set produced from the operation shown in FIG. 15.

To achieve the pattern shown in FIG. 15, the electrode in common (electrode 1) could be selected as a transmitter electrode or as a receiver electrode. In this embodiment, electrode 1 is selected as a transmitter electrode for each coupling operation, as represented by the arrow on each of the field lines. Thus, in an embodiment, the procedures are initiated by energizing electrode 1 and monitoring electrode 2 to produce a first electric field 1501. Electrode 1, as the electrode in common, is energized again but with electrode 3 being monitored, to produce a second electric field 1502. Again, as the electrode in common, electrode 1 is energized and a third electric field 1503 is produced by monitoring electrode 4. This process is repeated with respect to electrode 5 being monitored, electrode 6 being monitored, electrode 7 being monitored and electrode 8 being monitored, producing respective electric fields 1504 to 1507.

FIG. 16

The procedures described with reference to FIG. 15 produce a common electrode data set 1601. This is made up of seven coupling data sets 1611 to 1617, from the first transmitter electrode 1 coupling with seven receiver electrodes 2 to 8. In addition, as the distance between the electrodes increases, the degree of layering also increases. Thus, the first coupling data set 1611 may be identified as belonging to layer one, with the second belonging to layer two, the third belonging to layer three and so on, with the seventh 1617 relating to layer seven.

As described with reference to FIG. 14, each coupling data set consists of five data samples 1411 to 1415.

FIG. 17

In this embodiment, the systematic selection of electrodes started by selecting a first end electrode, electrode 1, as an electrode in common to produce the first common electrode data set 1601. The process continues by sequentially selecting adjacent electrodes as electrodes in common in a first direction of dynamic layering, until a second end electrode (electrode 15 in this example) is reached.

Thus, in accordance with this embodiment, having selected electrode 1 as the electrode in common, adjacent electrode 2 is now selected as the electrode in common, resulting in the generation of electric fields 1701 to 1707.

FIG. 18

Figure 17:
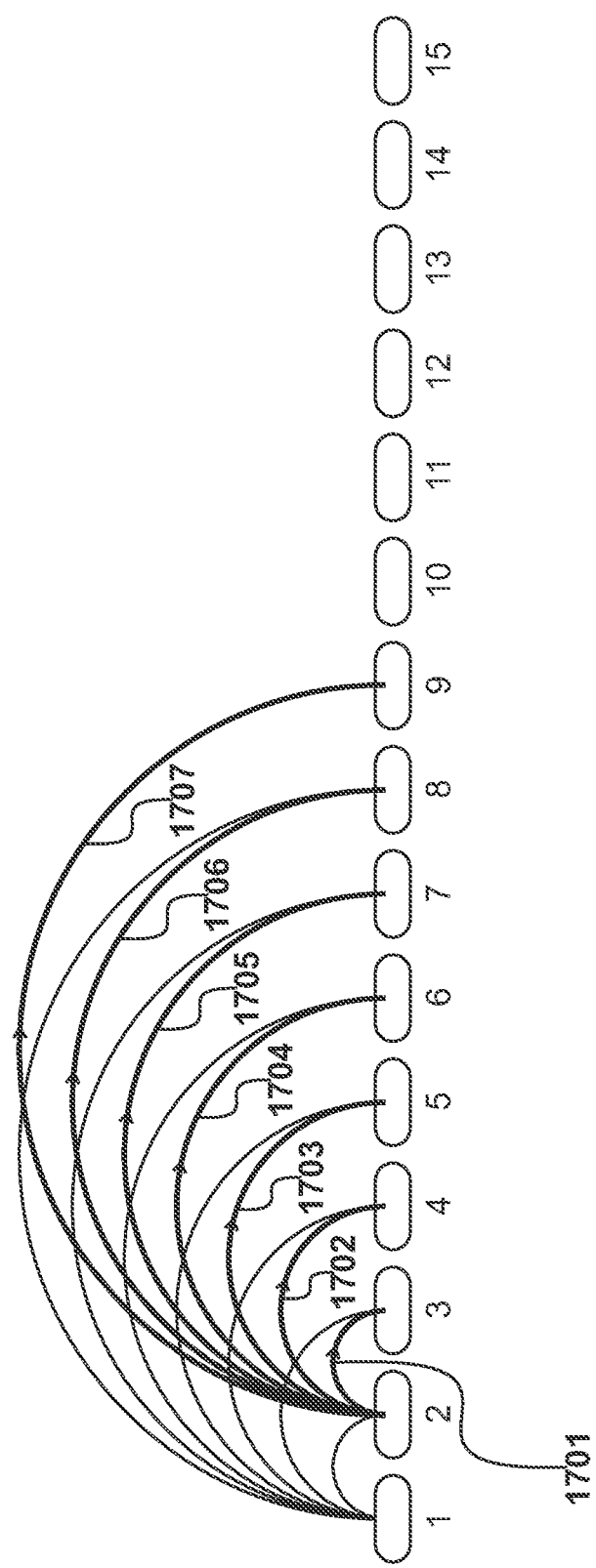
FIG. 17 illustrates the energization of a second electrode.
Figure 18:
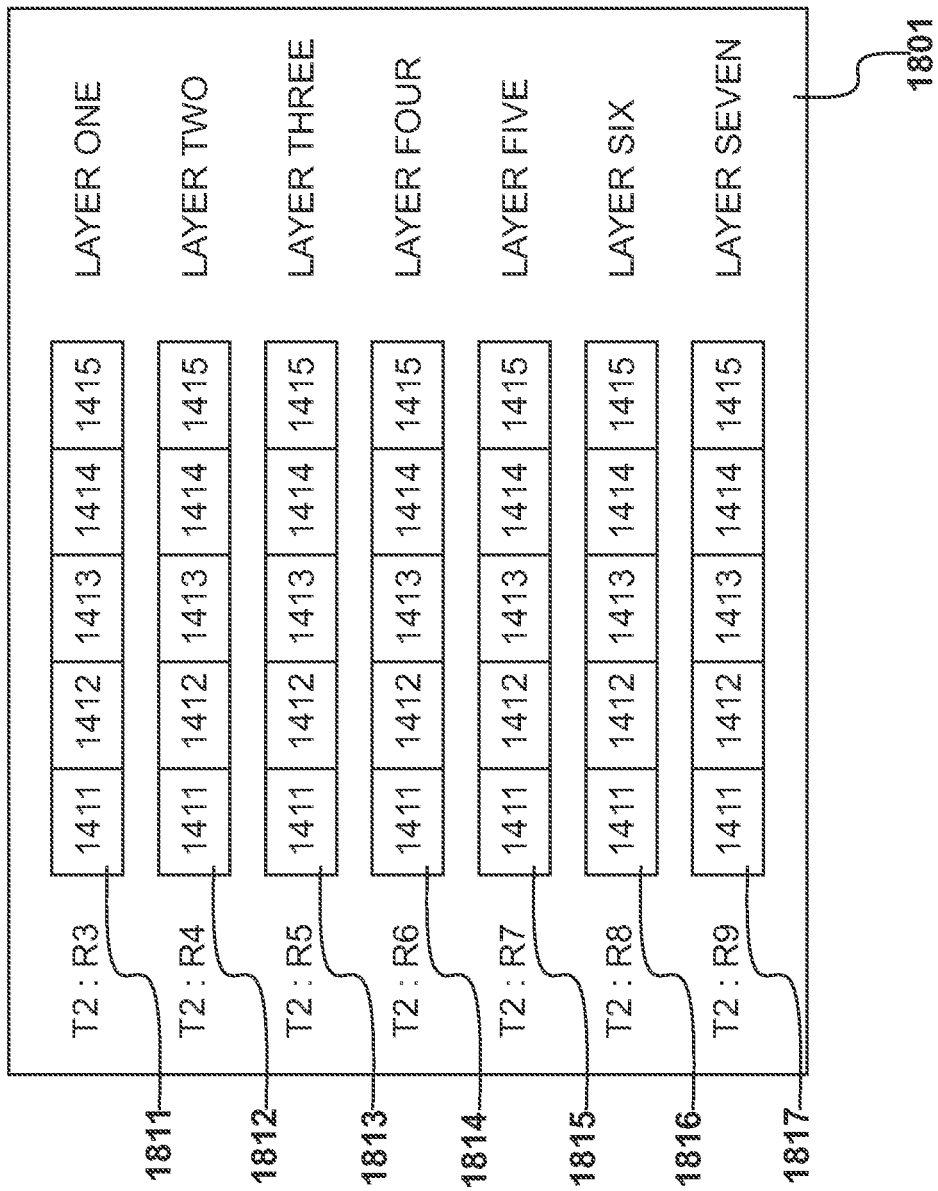
FIG. 18 illustrates a common electrode data set produced from the operations illustrated in FIG. 17.

The coupling operations illustrated in FIG. 17, result in the production of a second common electrode data set 1801. Again, this produces a further seven coupling data sets 1811 to 1817, representing the seven layers of penetration, each again including five coupling data sets 1401 to 1405.

FIG. 19

Figure 19:
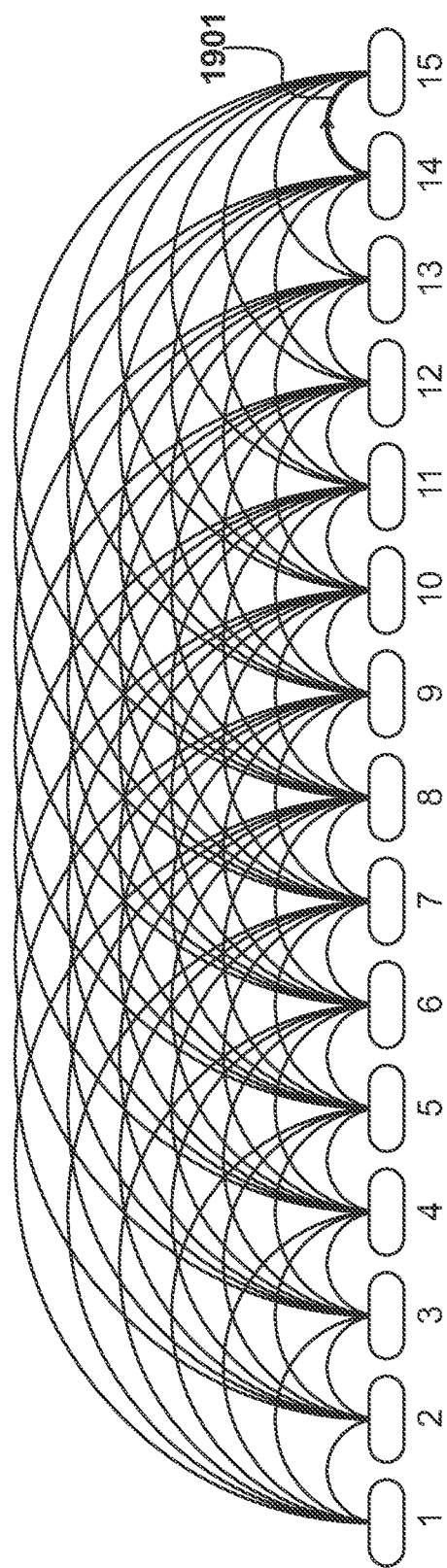
FIG. 19 continues to illustrate a process of sequentially selecting adjacent electrodes as electrodes in common.

The process of sequentially selecting adjacent electrodes as electrodes in common continues until a second end electrode is reached, as illustrated in FIG. 19. When electrode 8 is selected as the electrode in common, a full seven layers of penetration can be achieved, giving the couplings that are possible with electrodes 9 to 15. However, as subsequent electrodes are selected as the electrode in common, the level of penetration reduces until, as shown in FIG. 19, when electrode 14 is selected as the electrode in common it is only possible for it to couple with electrode 15, as illustrated by electric field 1901.

FIG. 20

Figure 20:
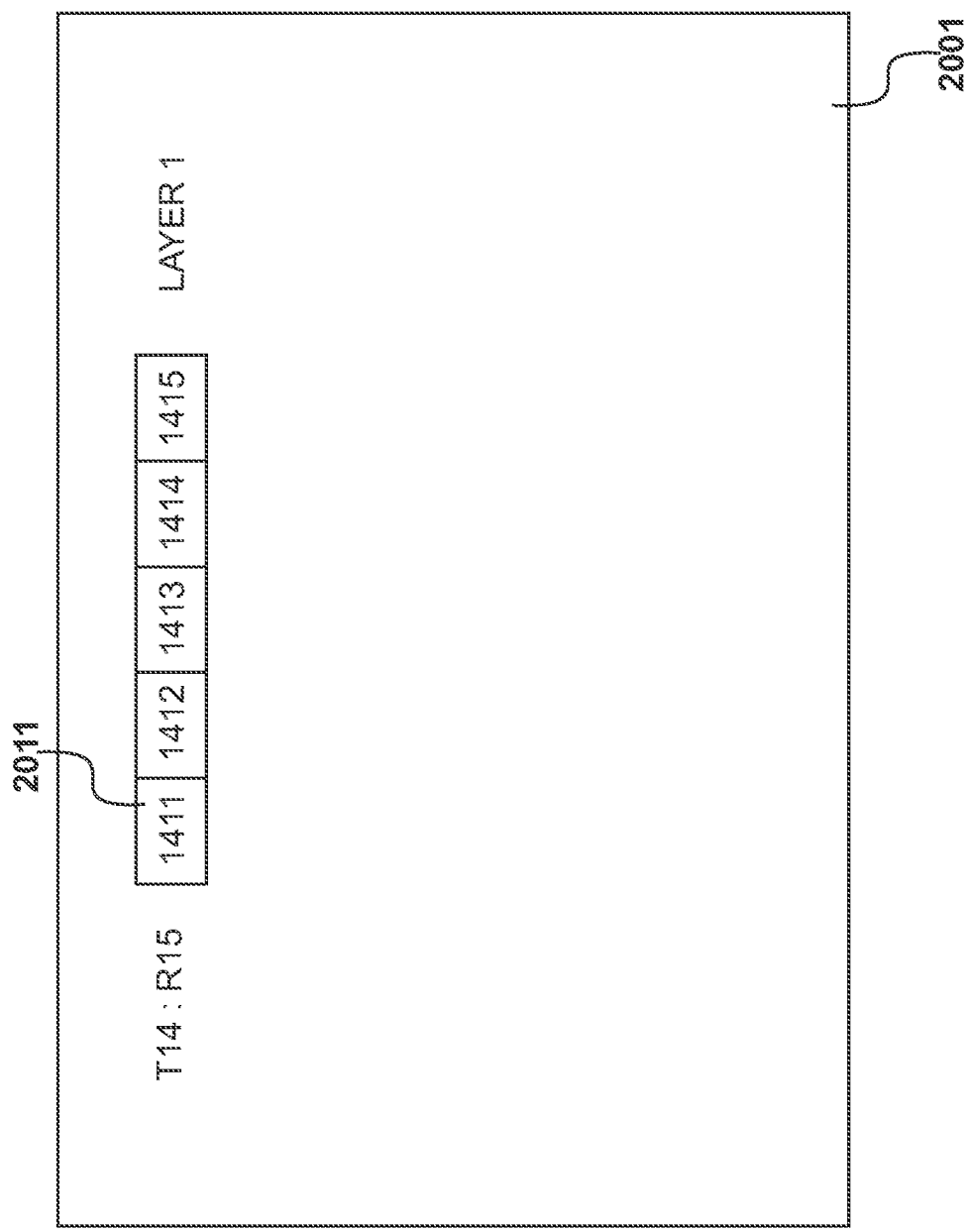
FIG. 20 illustrates data produced from the energization of electrode 14.

As illustrated in FIG. 20, when electrode 14 is selected as the electrode in common, only one common electrode data set is produced. Again, this common electrode data set consists of five coupling data sets 1401 to 1405.

FIG. 21

Figure 21:
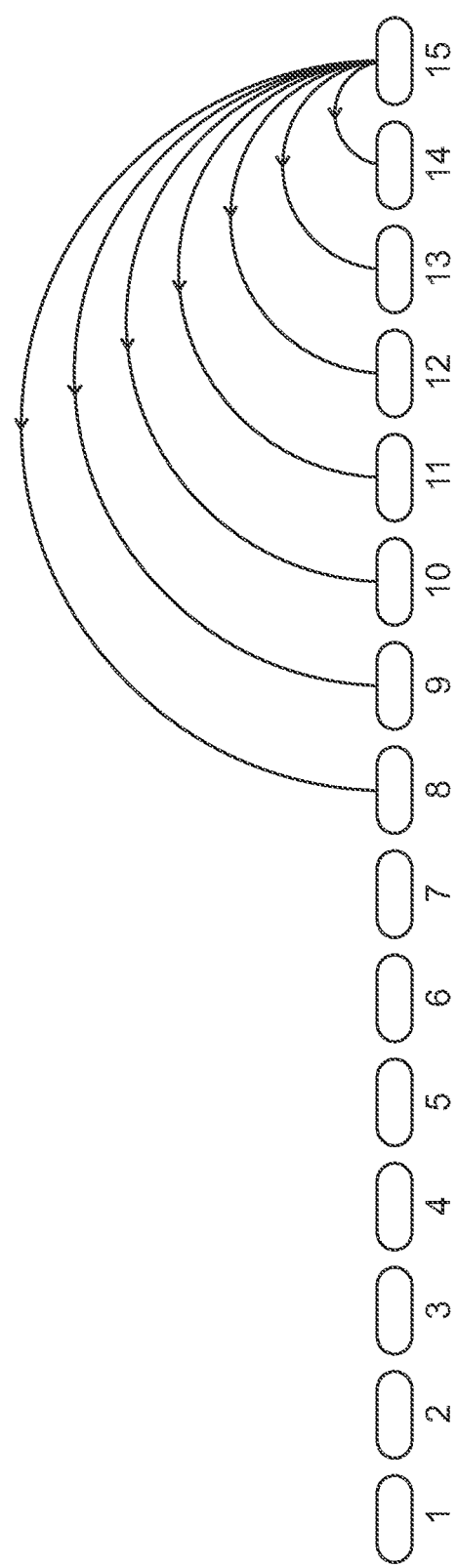
FIG. 21 illustrates the start of reverse layering from electrode 15.
Figure 22:
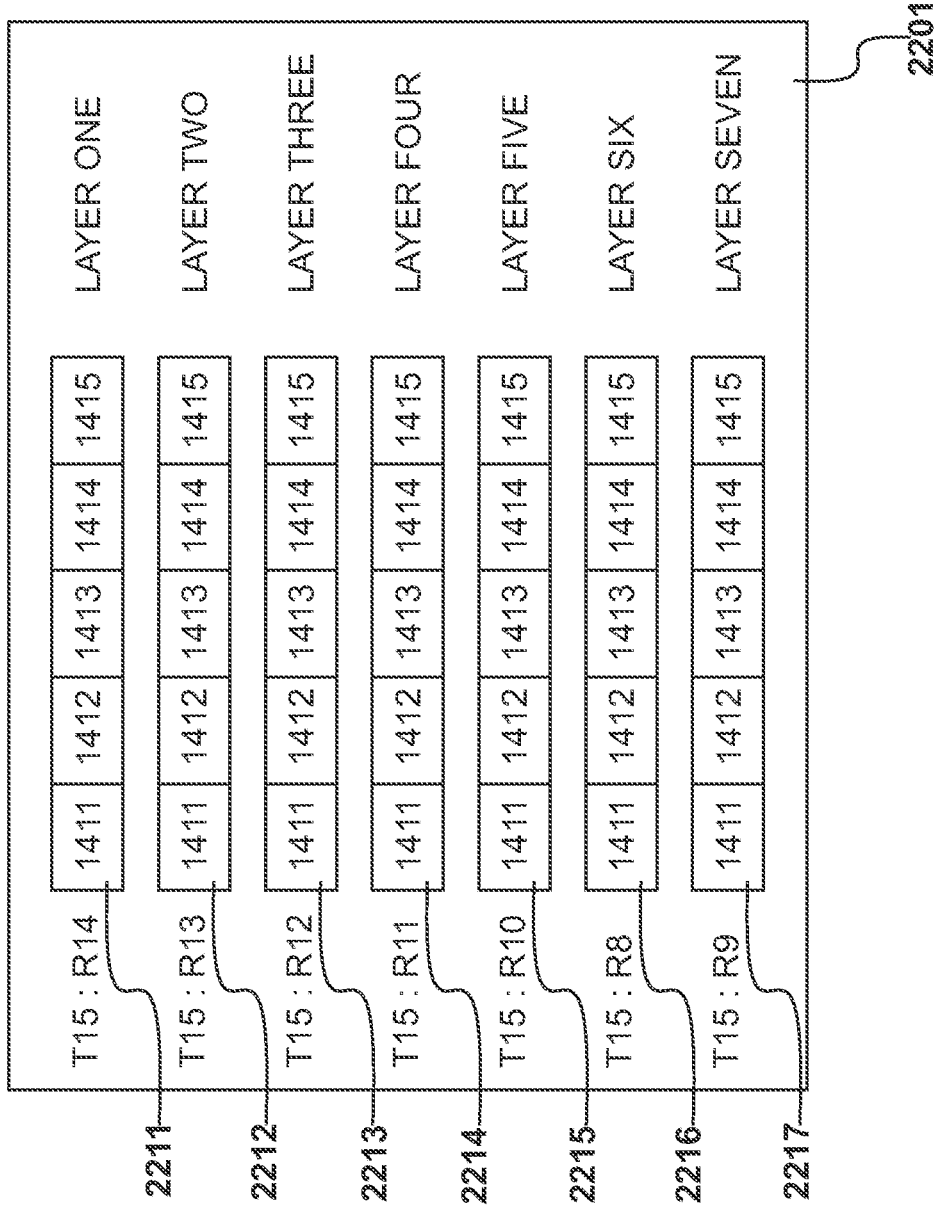
FIG. 22 shows a common electrode data set by reverse layering.

After reaching the second end electrode, as described with reference to FIG. 19, the second end electrode 15 is now selected as an electrode in common, as shown in FIG. 21. From this, adjacent electrodes are again sequentially selected as the electrode in common, moving in the second direction of dynamic layering until the first end is reached. Thus, for each selected electrode in common, such as electrode 15 in FIG. 21, a second set of m electrodes are selected that are the nearest neighbours (14 to 8), but only in the direction of dynamic layering.

FIG. 22

The procedures described with reference to FIG. 21 produce a new common electrode data set 2201. Again, on this occasion, penetration is possible to level seven, resulting in the generation of seven coupling data sets 2211 to 2217.

FIG. 23

Figure 23:
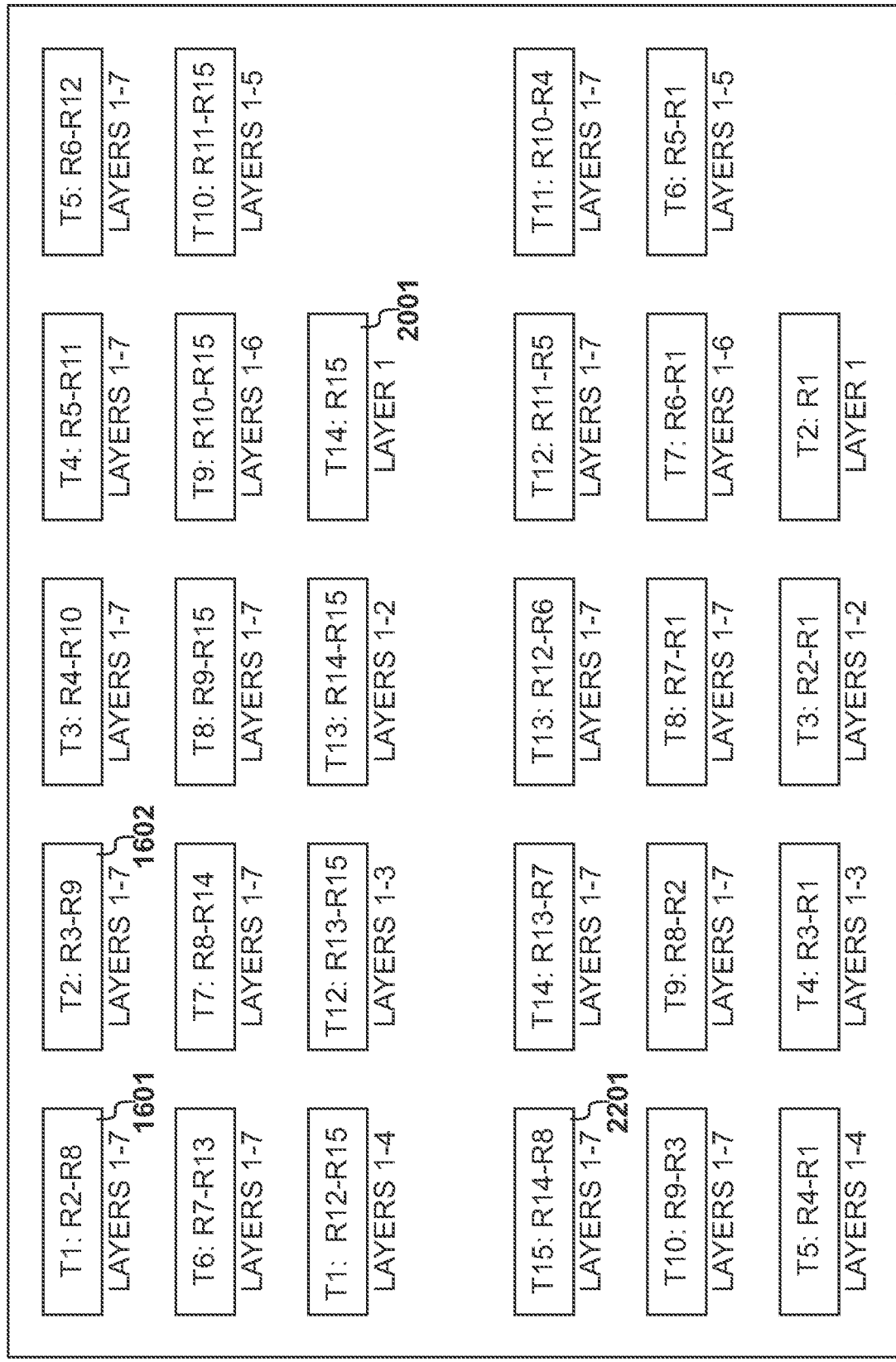
FIG. 23 shows a layering data set.

As illustrated in FIG. 23, the complete cycle of forward dynamic layering followed by reverse dynamic layering produces twenty-eight common electrode data sets, which include common electrode data sets 1601, 1602, 2001 and 2201, along with all the others making up a complete layering data set 2301.

The result, as shown in FIG. 23, is the production of the first group layering data. For a complete scan, to produce the output data block 1001, the procedures are performed again for the calibration first group layering data, the calibration second group layering data and the test second group layering data 1007.

FIG. 24

Each of the common electrode data sets illustrated in FIG. 23, includes data relating to different layers. Consequently, it is possible to reorganise this data to assemble each coupling data set with reference to its layer of penetration.

Figure 24:
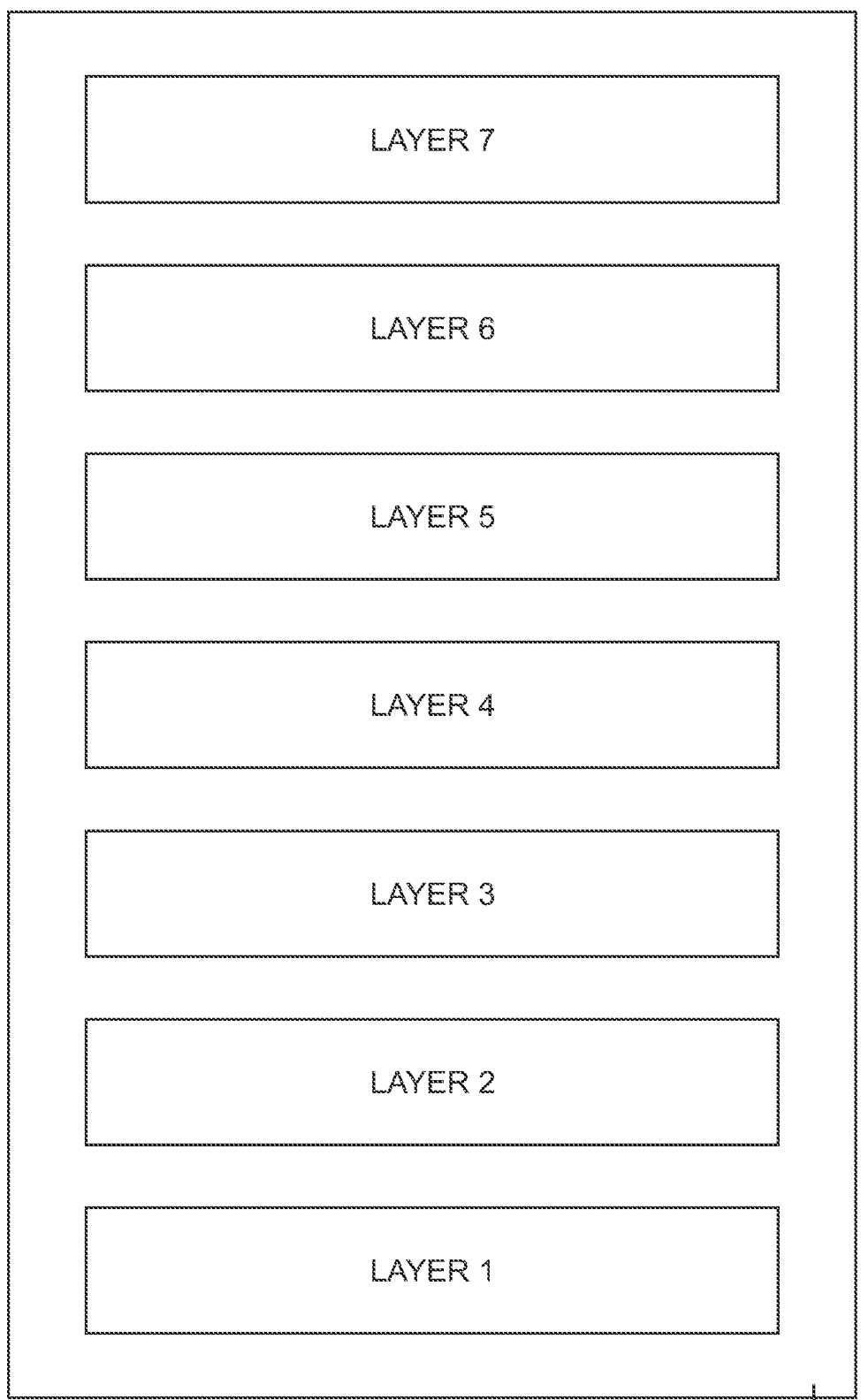
FIG. 24 illustrates a rearrangement of data to identify individual layers.

In FIG. 24, the totality of the data is still the layering data set 2301. However, the data has been reorganized to collect each coupling data set that relates to one of the layers, consisting of layer one to layer seven.

FIG. 25

The layer seven data identified in FIG. 24 is shown in greater detail in FIG. 25. In this embodiment, a coupling data set, consisting of sample points 1401 to 1405 are present for eight coupling operations, in which electrode 1, couples with electrode 8, through to electrode 8 coupling with electrode 15.

Such a rearrangement of the data may facilitate deep learning exercises that identify appropriate relationships to gain a better understanding of the way in which the properties of the objects change.

I claim:

1. An apparatus for examining an object using electric fields to identify regions in said object of differing permittivity and conductivity, comprising:
a plurality of substantially parallel electrodes mounted on a substrate, wherein said plurality of substantially parallel electrodes are coated with an insulator allowing said plurality of substantially parallel electrodes to be brought into contact with said object and thereby be in capacitive alignment with said object;
a generator for generating energization pulses and a de-multiplexer for applying said energization pulses to any of said plurality of substantially parallel electrodes as a transmitter electrode;
a monitor for monitoring output signals and a multiplexer for connecting any one of said plurality of substantially parallel electrodes to said monitor; and
a processor, wherein said processor is configured to:
select a first set of n electrodes from said plurality of substantially parallel electrodes; and
establish capacitively coupled electrode pairs, in which each of said first set of n electrodes is capacitively coupled with a second set of m electrodes from said plurality of substantially parallel electrodes, wherein:
each said second set of m electrodes are nearest neighbouring electrodes to an electrode selected from said first set of n electrodes; and
the number of electrodes present in said second set of m electrodes represents a degree of layering.

2. The apparatus of claim 1, further comprising an energizing circuit for energizing said transmitter electrode to a level determined by said processor, wherein said processor adjusts a level of energizing with reference to the degree of layering.

3. The apparatus of claim 1, further comprising an analog-to-digital converter for sampling said output signals, to produce an output data set.

4. The apparatus of claim 3, further comprising:
a storage device for storing said output data set; and
a transmission device for transmitting said output data set.

5. The apparatus of claim 4, further comprising a machine-learning system for receiving said output data set to produce extent data for a substance of interest present within said object.

6. A method of examining an object using electric fields to identify regions in said object of differing permittivity and conductivity, comprising the steps of:
deploying a plurality of substantially parallel electrodes in capacitive alignment with said object;
generating energization pulses for application to any of said plurality of substantially parallel electrodes as a transmitter electrode;
monitoring output signals from any remaining one of said plurality of substantially parallel electrodes as a receiver electrode, wherein a peak value of an output signal is indicative of permittivity and a decay rate of said output signal is indicative of conductivity, such that during each energization operation, an energized transmitter electrode and a monitored receiver electrode define a capacitively coupled electrode pair;
selecting a first set of n electrodes from said plurality of substantially parallel electrodes; and
establishing capacitively coupled electrode pairs, in which each of said first set of n electrodes is capacitively coupled with a second set of m electrodes from said plurality of substantially parallel electrodes, wherein:
each said second set of m electrodes are nearest neighbouring electrodes to an electrode selected from said first set of n electrodes; and
the number of electrodes present in said second set of m electrodes represents a degree of layering.

7. The method of claim 6, wherein said step of establishing capacitively coupled electrode pairs comprises the steps of:
sequentially selecting each n electrode of said first set of n electrodes as an electrode in common; and
for each said electrode in common, sequentially defining capacitively coupled electrode pairs with a second set of m nearest neighbouring electrodes.

8. The method of claim 7, wherein said step of sequentially selecting each n electrode of said first set of n electrodes comprises the steps of:
selecting a first end electrode as an electrode in common;
sequentially selecting adjacent electrodes as electrodes in common in a first direction of dynamic layering until a second end electrode is reached;
selecting said second end electrode as an electrode in common;
sequentially selecting adjacent electrodes as electrodes in common in a second direction of dynamic layering until said first end electrode is reached; and
selecting a set of m electrodes for each electrode in common that are nearest neighbours only in at least one of said first direction of dynamic layering or said second direction of dynamic layering.

9. The method of claim 6, further comprising the step of sampling each output signal of said output signals produced from each capacitively coupled electrode pair to produce a coupling data set, wherein a first sample of each said coupling data set is indicative of permittivity and subsequent samples of each said coupling data set are indicative of conductivity.

10. The method of claim 9, wherein each said coupling data set is associated with a degree of layering.

11. The method of claim 6, wherein said step of selecting said first set of n electrodes comprises the step of selecting all of said plurality of substantially parallel electrodes.

12. The method of claim 6, wherein said step of selecting said first set of n electrodes comprises the steps of:
identifying capacitively aligned electrodes that are at a position of said object; and
selecting said capacitively aligned electrodes as said first set of n electrodes.

13. The method of claim 6, wherein:
said plurality of substantially parallel electrodes represents a first group of substantially parallel electrodes;
a further layering procedure is performed with respect to a second group of substantially parallel electrodes; and
said second group is substantially orthogonal to said first group.

14. The method of claim 6, wherein a first layering procedure is performed with no object present to generate calibration data, prior to similar layering procedures being performed when said object is present to produce test data.

15. The method of claim 14, further comprising the steps of:
    producing plural learning output data sets for a first group of objects, for which an extent to which a substance under investigation is present is known;
    deploying said plural learning output data sets to prepare a machine-learning system; and
    analysing live output data sets by said machine-learning system to produce respective extent data for said substance.

* * * * *